(12) United States Patent
Pisharodi

(10) Patent No.: US 9,198,774 B2
(45) Date of Patent: Dec. 1, 2015

(54) INTERVERTEBRAL DISK CAGE AND STABILIZER

(71) Applicant: Perumala Corporation, Brownsville, TX (US)

(72) Inventor: Madhavan Pisharodi, Brownsville, TX (US)

(73) Assignee: Perumala Corporation, Brownsville, TX (US)

(*) Notice: Subject to any disclaimer, the term of this patent is extended or adjusted under 35 U.S.C. 154(b) by 0 days.

(21) Appl. No.: 14/086,398

(22) Filed: Nov. 21, 2013

(65) Prior Publication Data

US 2015/0142114 A1    May 21, 2015

(51) Int. Cl.
*A61F 2/44* (2006.01)
*A61F 2/46* (2006.01)
*A61F 2/30* (2006.01)

(52) U.S. Cl.
CPC .............. *A61F 2/4455* (2013.01); *A61F 2/447* (2013.01); *A61F 2/4611* (2013.01); *A61F 2/4637* (2013.01); *A61F 2002/30367* (2013.01); *A61F 2002/30517* (2013.01); *A61F 2002/30576* (2013.01); *A61F 2002/30579* (2013.01); *A61F 2002/30879* (2013.01); *A61F 2002/448* (2013.01); *A61F 2002/4475* (2013.01); *A61F 2002/4627* (2013.01); *A61F 2002/4638* (2013.01)

(58) Field of Classification Search
CPC ....... A61F 2/4455; A61F 2/446; A61F 2/447; A61F 2/44; A61F 2002/4475; A61F 2002/448; A61F 2002/4638

USPC .................. 623/17.11, 17.15, 17.16
See application file for complete search history.

(56) References Cited

U.S. PATENT DOCUMENTS

| | | | |
|---|---|---|---|
| 5,653,761 A | 8/1997 | Pisharodi | |
| 5,653,762 A | 8/1997 | Pisharodi | |
| 5,658,336 A | 8/1997 | Pisharodi | |
| 5,669,909 A * | 9/1997 | Zdeblick et al. | 606/247 |
| 5,683,394 A * | 11/1997 | Rinner | A61F 2/4455 606/247 |
| 5,683,463 A * | 11/1997 | Godefroy et al. | 623/17.16 |
| 5,702,391 A * | 12/1997 | Lin | 623/17.11 |
| 5,893,890 A | 4/1999 | Pisharodi | |
| 6,159,244 A * | 12/2000 | Suddaby | 623/17.11 |
| 6,179,873 B1 * | 1/2001 | Zientek | 623/17.11 |
| 6,206,922 B1 * | 3/2001 | Zdeblick et al. | 623/17.11 |
| 6,251,140 B1 * | 6/2001 | Marino et al. | 623/17.16 |
| 6,290,724 B1 * | 9/2001 | Marino | 623/17.11 |
| 6,309,421 B1 | 10/2001 | Pisharodi | |
| 6,325,827 B1 * | 12/2001 | Lin | A61B 17/025 623/17.16 |
| 6,371,988 B1 * | 4/2002 | Pafford et al. | 623/17.11 |
| 6,447,544 B1 * | 9/2002 | Michelson | 623/17.16 |
| 6,602,256 B1 * | 8/2003 | Hayes | 606/296 |
| 6,610,089 B1 * | 8/2003 | Liu et al. | 623/17.11 |
| 6,666,889 B1 * | 12/2003 | Commarmond | 623/17.11 |
| 6,835,206 B2 * | 12/2004 | Jackson | 623/17.11 |
| 6,926,737 B2 * | 8/2005 | Jackson | 623/17.16 |
| 7,621,938 B2 * | 11/2009 | Molz, IV | 606/246 |
| 7,867,276 B2 * | 1/2011 | Matge et al. | 623/17.11 |

(Continued)

*Primary Examiner* — Matthew Lawson
*Assistant Examiner* — Amy Sipp
(74) *Attorney, Agent, or Firm* — D'Ambrosio & Menon, PLLC; Usha Menon

(57) ABSTRACT

A middle-expanded, removable intervertebral disk cage and stabilizer for stabilizing adjacent vertebrae and a method for intervertebral disk stabilization in which adjacent vertebrae are spread and a portion of the intervertebral disk is removed from between the adjacent vertebrae.

9 Claims, 29 Drawing Sheets

(56) References Cited

U.S. PATENT DOCUMENTS

| | | | |
|---|---|---|---|
| 7,871,441 B2* | 1/2011 | Eckman | 623/17.11 |
| 8,137,405 B2* | 3/2012 | Kostuik et al. | 623/17.16 |
| 8,221,462 B2* | 7/2012 | Dwyer et al. | 606/249 |
| 8,317,866 B2* | 11/2012 | Palmatier et al. | 623/17.11 |
| 8,377,132 B2* | 2/2013 | Wing et al. | 623/17.15 |
| 8,480,740 B2 | 7/2013 | Pisharodi | |
| 8,480,742 B2 | 7/2013 | Pisharodi | |
| 8,491,656 B2* | 7/2013 | Schoedinger et al. | 623/17.16 |
| 8,545,562 B1* | 10/2013 | Materna et al. | 623/17.11 |
| 8,673,005 B1* | 3/2014 | Pimenta et al. | A61F 2/4455 623/17.11 |
| 8,814,912 B2* | 8/2014 | Carlson et al. | 606/264 |
| 8,900,310 B2* | 12/2014 | Carlson et al. | A61F 2/446 623/17.16 |
| 2002/0068976 A1* | 6/2002 | Jackson | 623/17.15 |
| 2002/0116065 A1* | 8/2002 | Jackson | 623/17.16 |
| 2002/0138146 A1* | 9/2002 | Jackson | 623/17.15 |
| 2003/0009224 A1* | 1/2003 | Kuras | 623/17.16 |
| 2003/0023306 A1* | 1/2003 | Liu et al. | 623/17.11 |
| 2004/0106996 A1* | 6/2004 | Liu et al. | 623/17.11 |
| 2005/0049590 A1* | 3/2005 | Alleyne et al. | A61F 2/442 623/17.11 |
| 2005/0065610 A1* | 3/2005 | Pisharodi | A61B 17/025 623/17.13 |
| 2005/0071009 A1* | 3/2005 | Muhanna et al. | 623/17.11 |
| 2005/0149195 A1* | 7/2005 | Boyd et al. | 623/17.11 |
| 2006/0064167 A1* | 3/2006 | Keller | 623/17.11 |
| 2007/0225706 A1* | 9/2007 | Clark et al. | 606/61 |
| 2008/0051901 A1* | 2/2008 | de Villiers et al. | 623/17.16 |
| 2008/0269902 A1* | 10/2008 | Baynham et al. | 623/17.16 |
| 2008/0288076 A1* | 11/2008 | Soo et al. | 623/17.16 |
| 2008/0312742 A1* | 12/2008 | Abernathie | 623/17.16 |
| 2009/0198337 A1* | 8/2009 | Phan | 623/17.16 |
| 2010/0070041 A1* | 3/2010 | Peterman et al. | 623/17.16 |
| 2010/0137988 A1* | 6/2010 | Markworth et al. | 623/17.16 |
| 2010/0211176 A1* | 8/2010 | Greenhalgh | 623/17.15 |
| 2011/0022176 A1* | 1/2011 | Zucherman et al. | 623/17.11 |
| 2011/0040382 A1* | 2/2011 | Muhanna | 623/17.11 |
| 2011/0077738 A1* | 3/2011 | Ciupik et al. | 623/17.11 |
| 2012/0016479 A1* | 1/2012 | Pisharodi | 623/17.16 |
| 2012/0071979 A1* | 3/2012 | Zipnick | 623/17.16 |
| 2013/0073045 A1* | 3/2013 | Vestgaarden | 623/17.16 |
| 2014/0039622 A1* | 2/2014 | Glerum et al. | 623/17.15 |
| 2014/0094919 A1* | 4/2014 | Mantri | 623/17.16 |

* cited by examiner

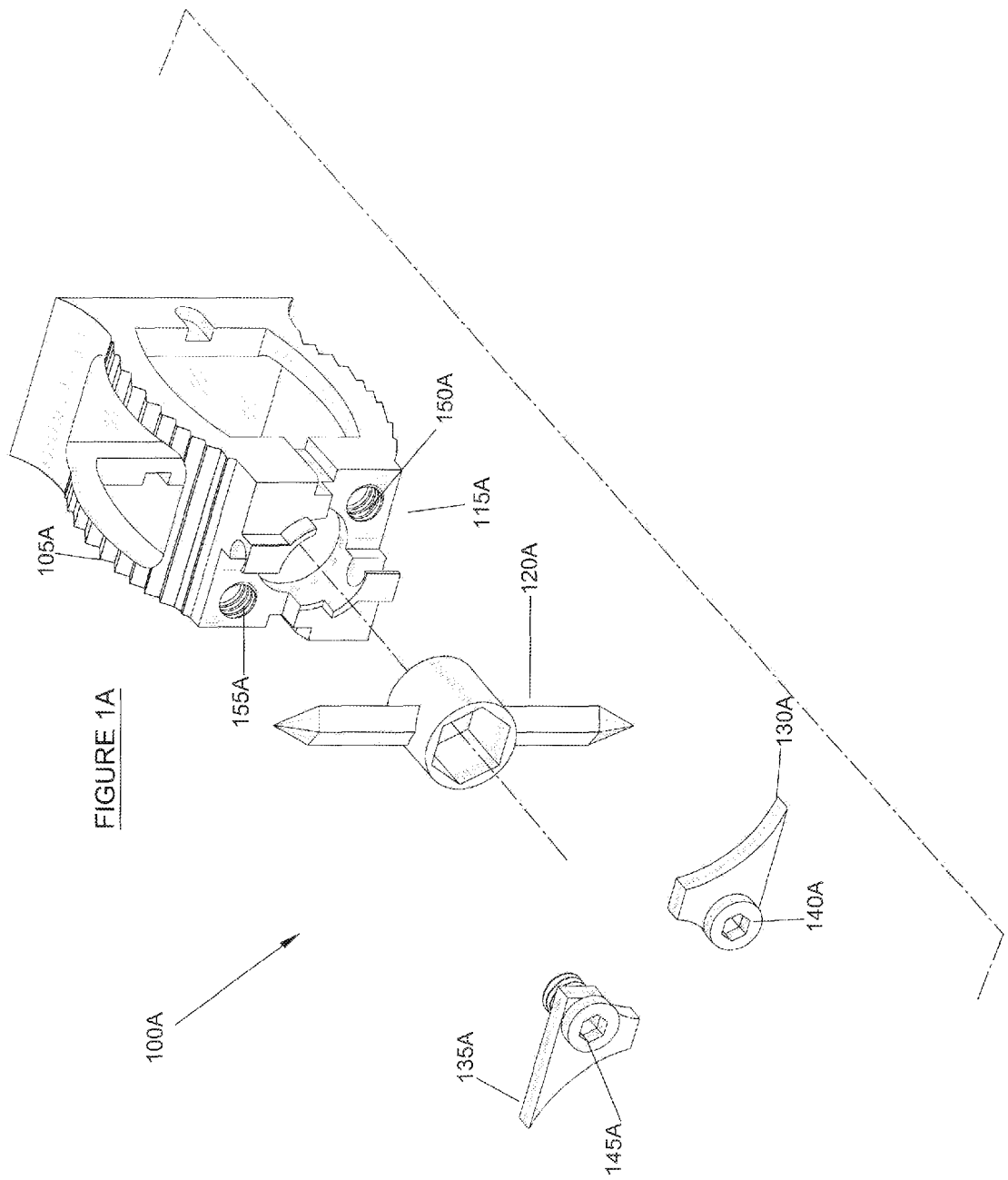

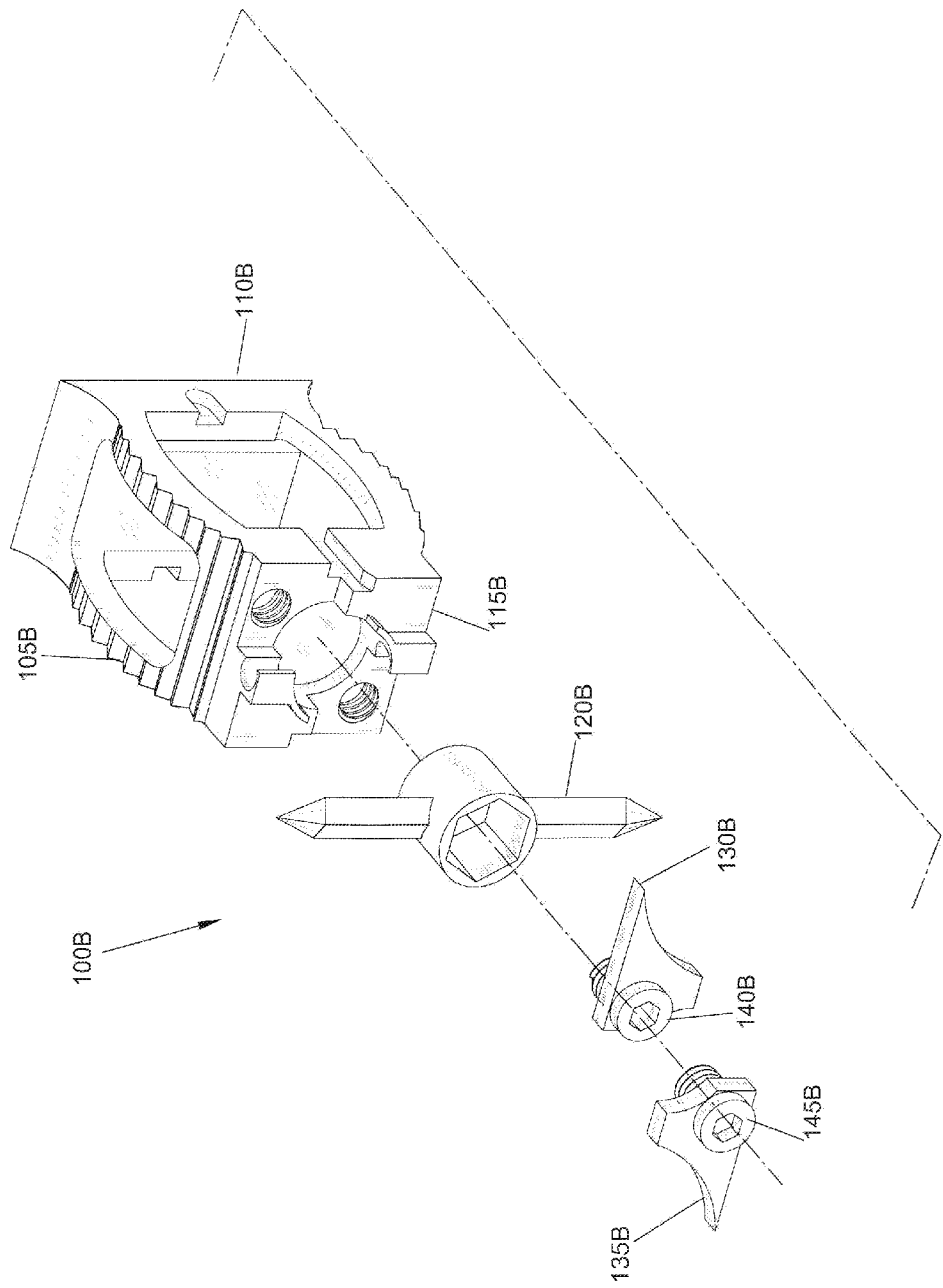

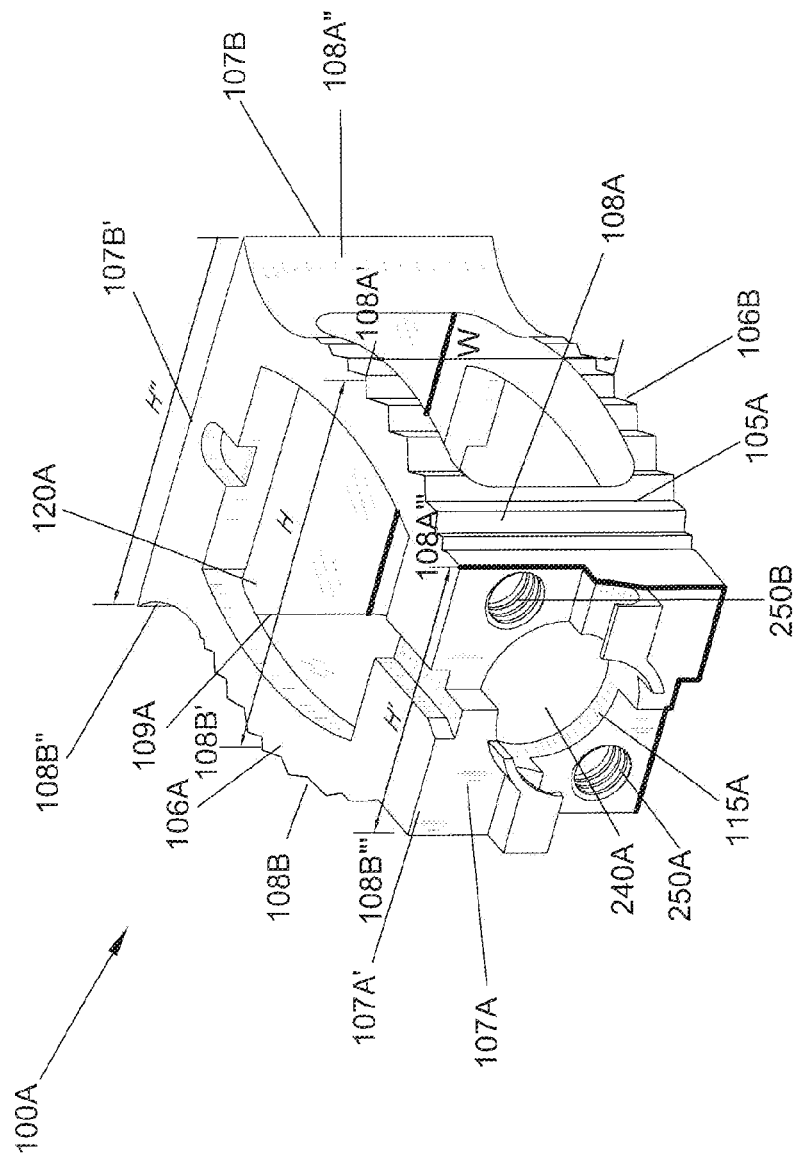

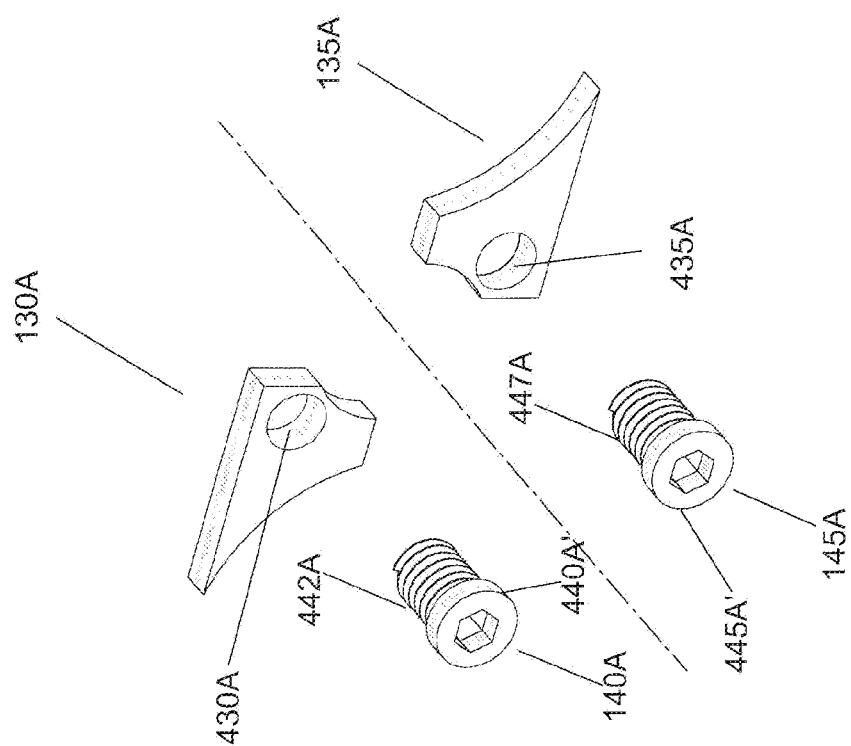

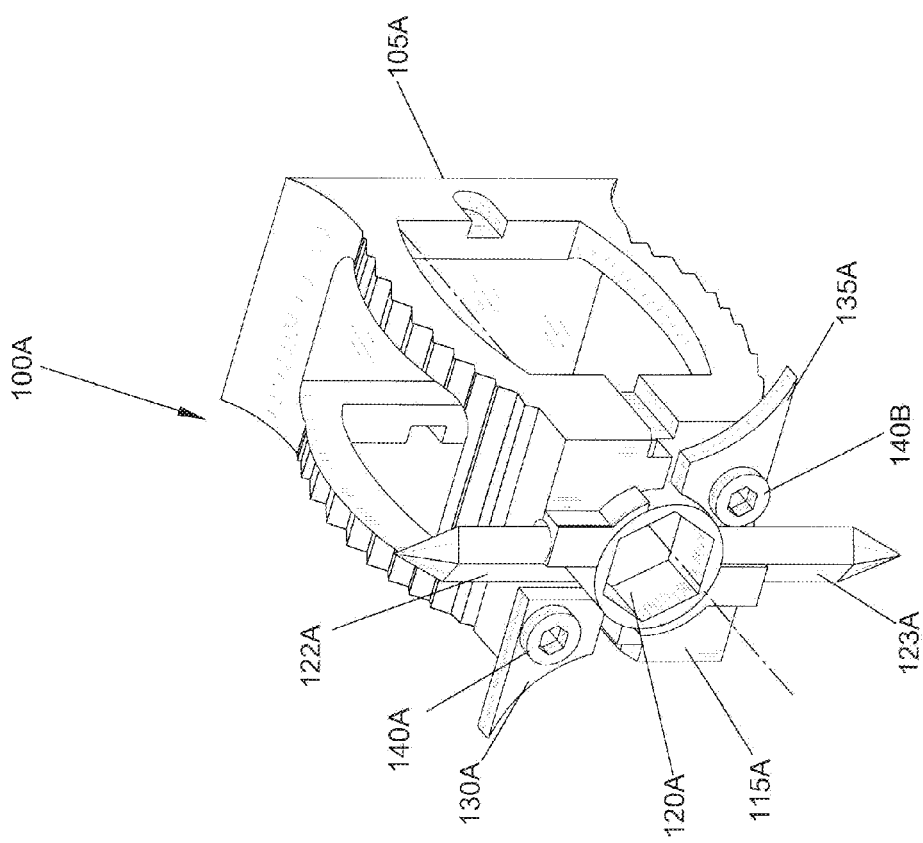

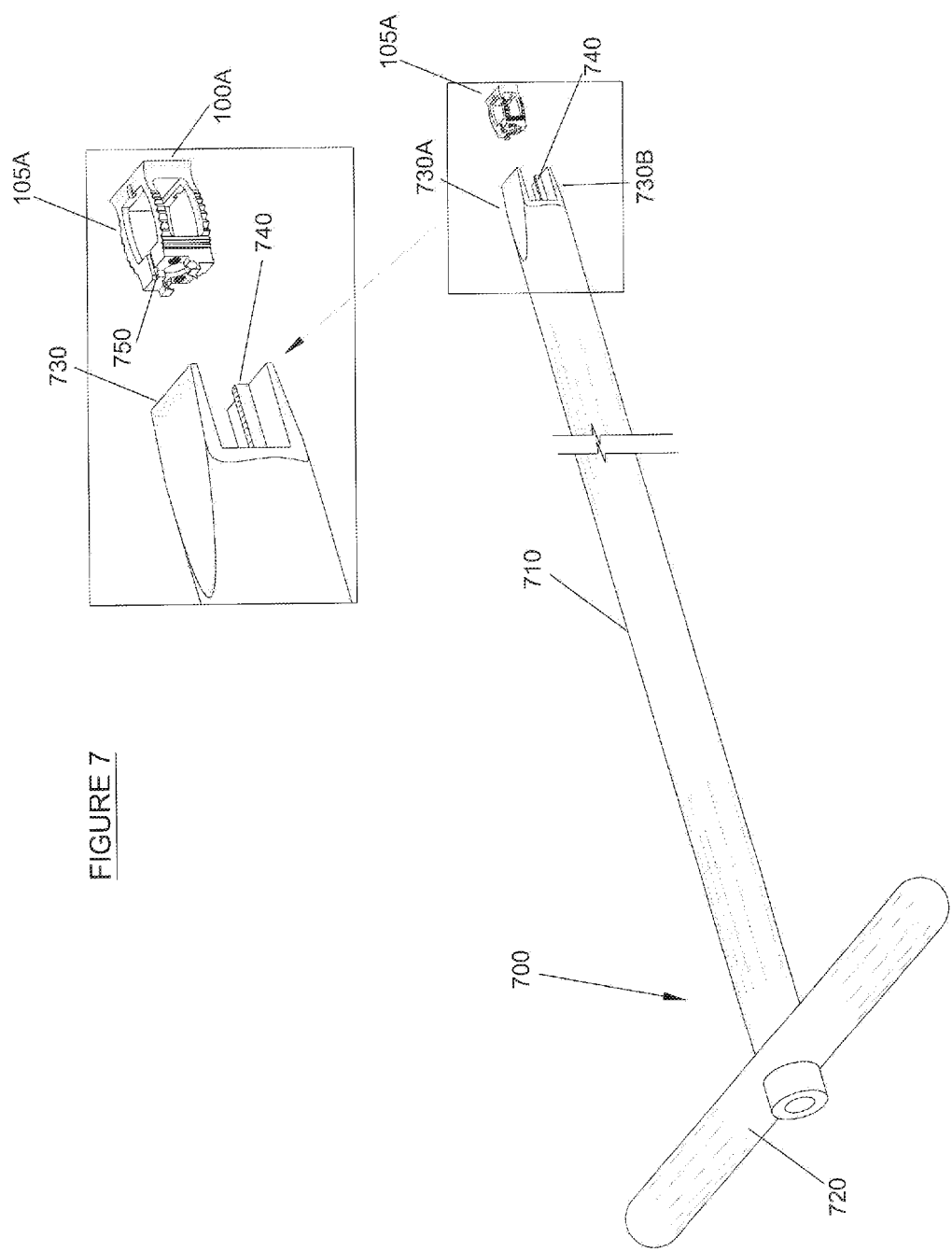

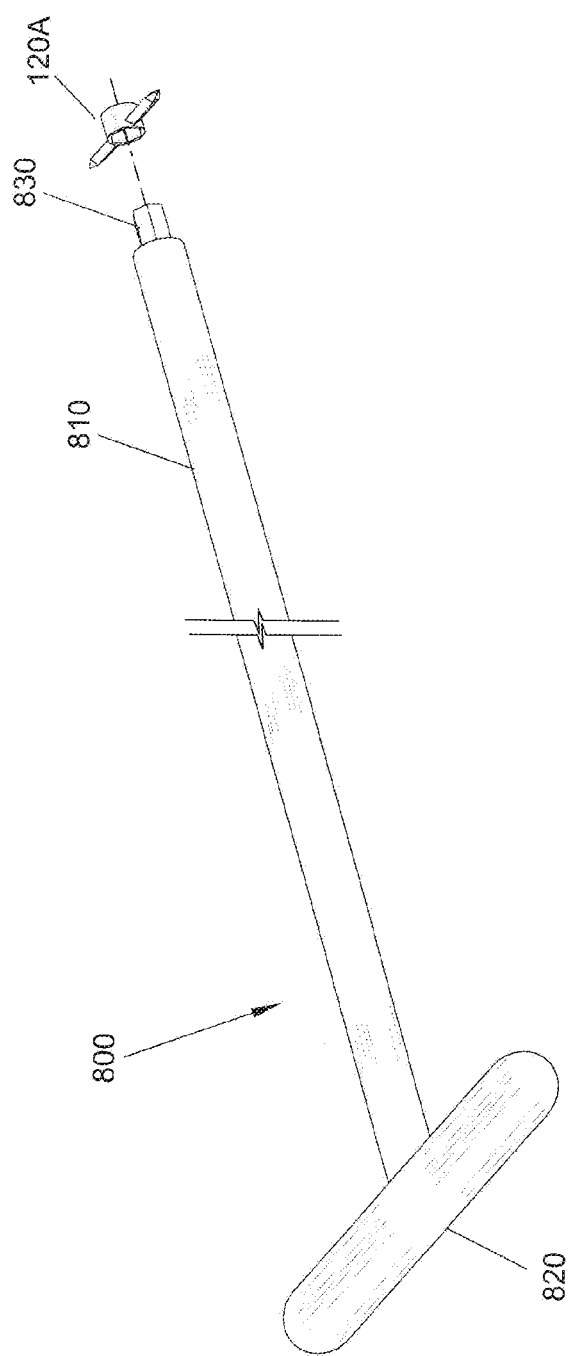

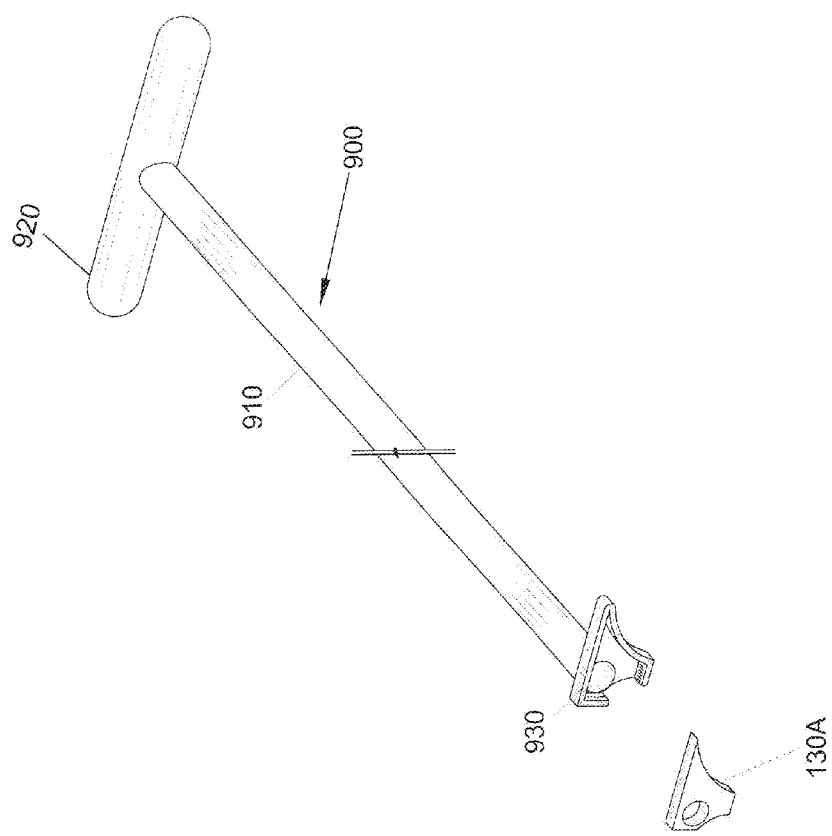

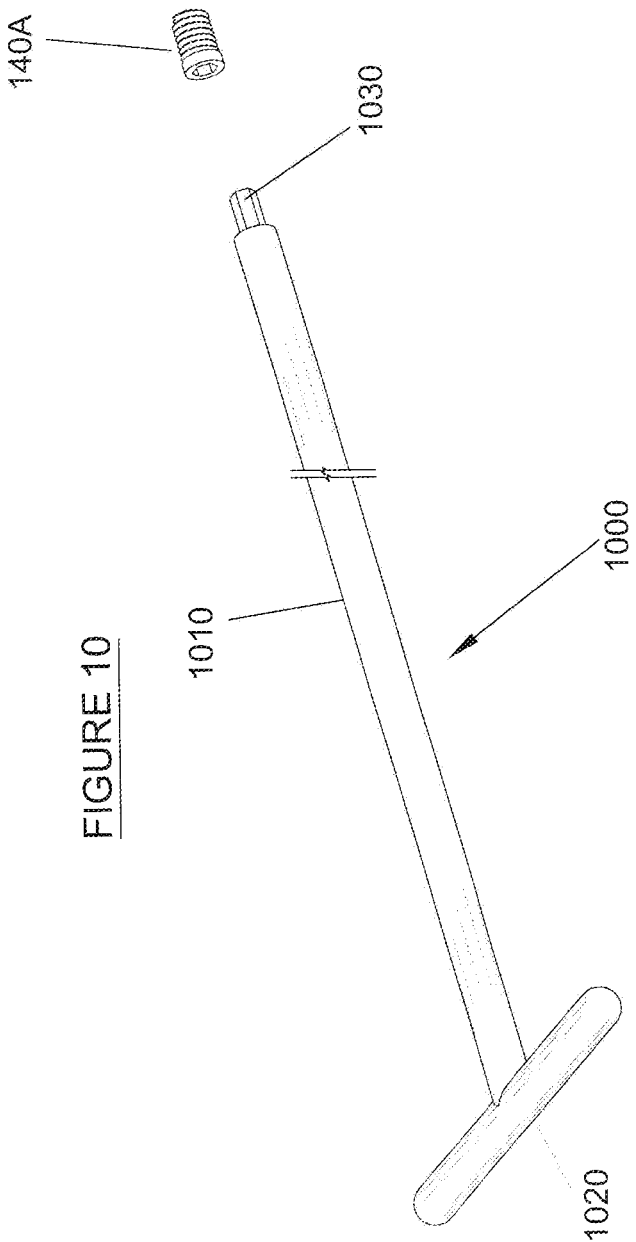

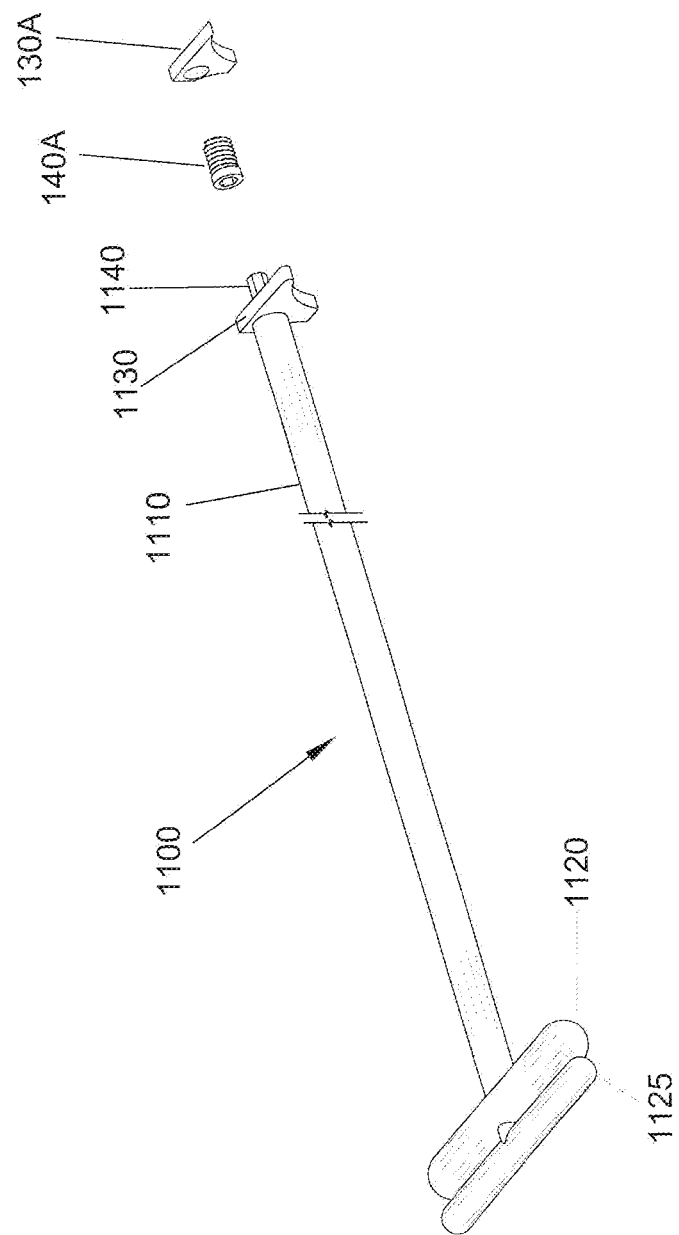

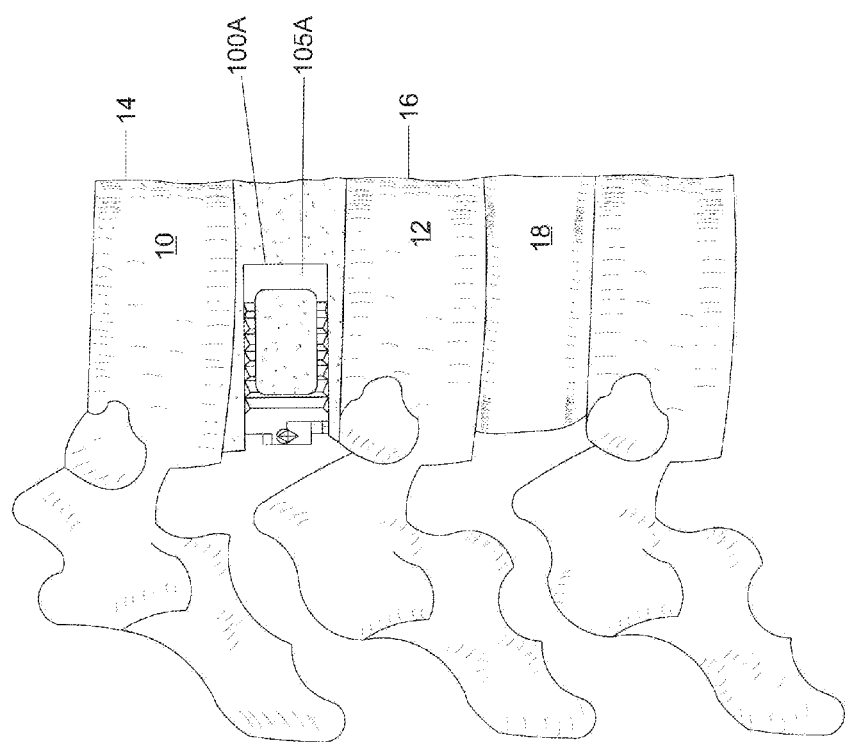

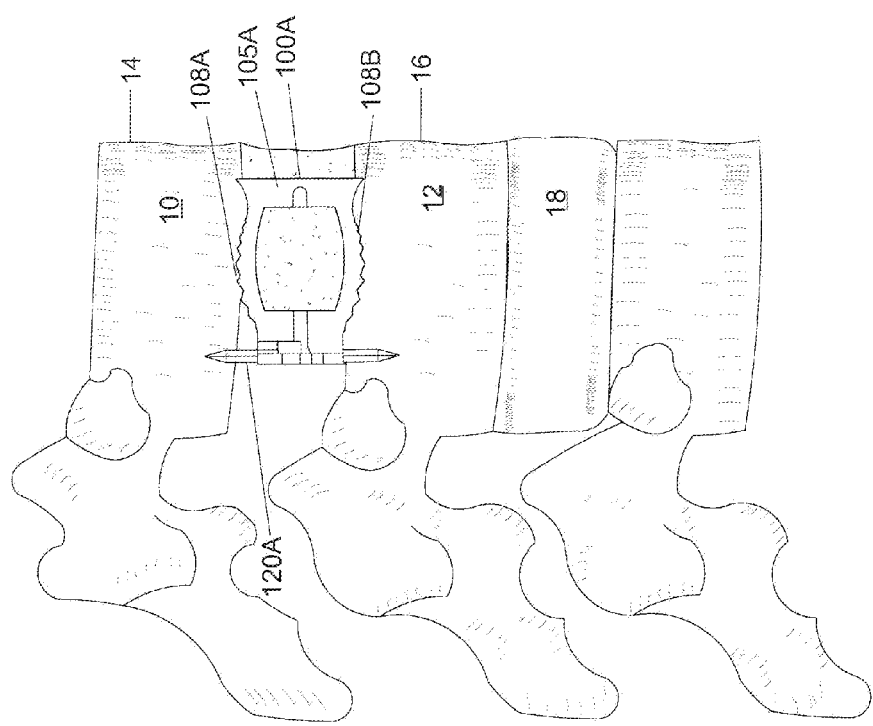

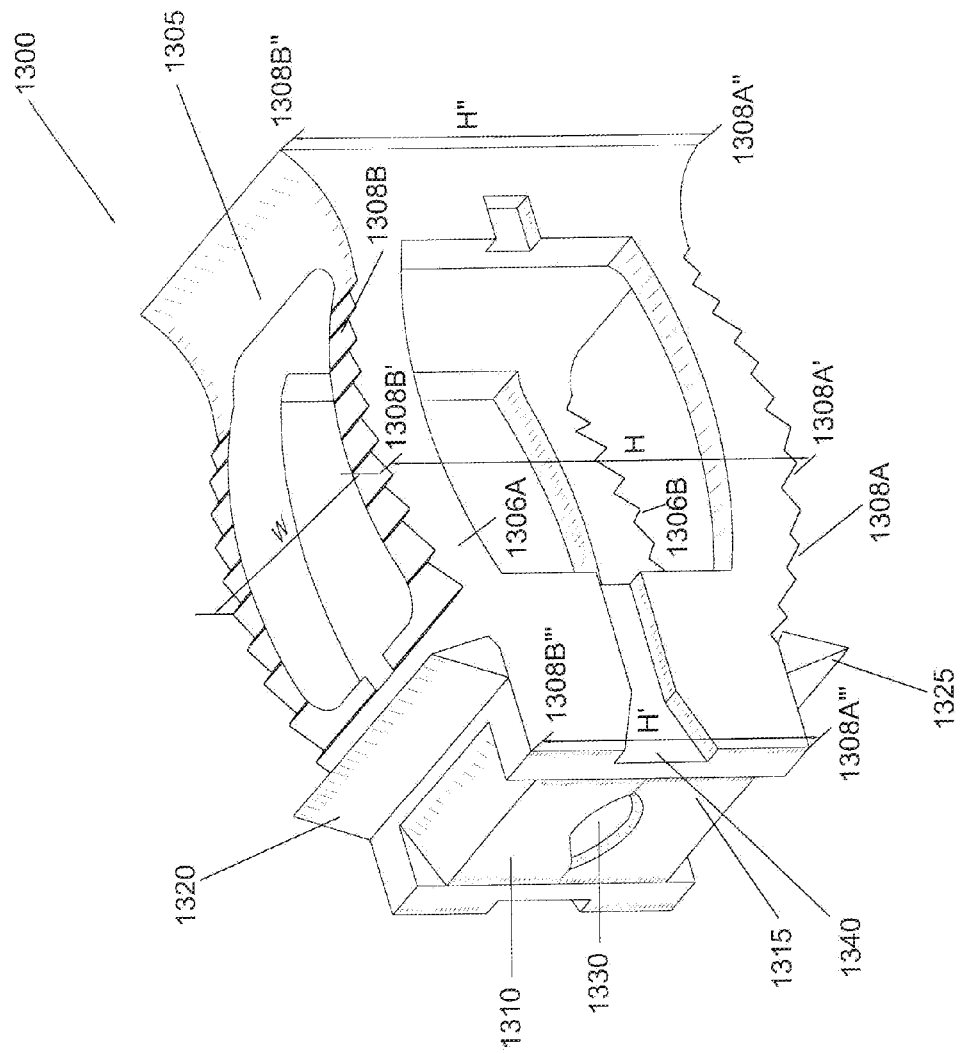

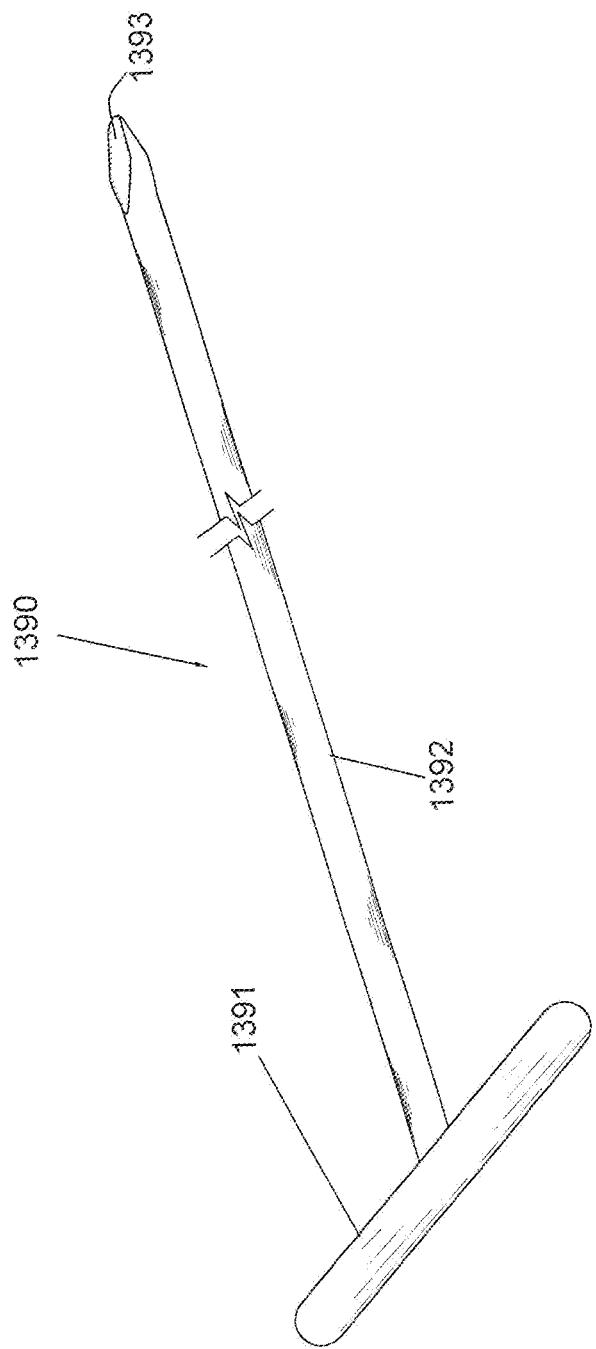

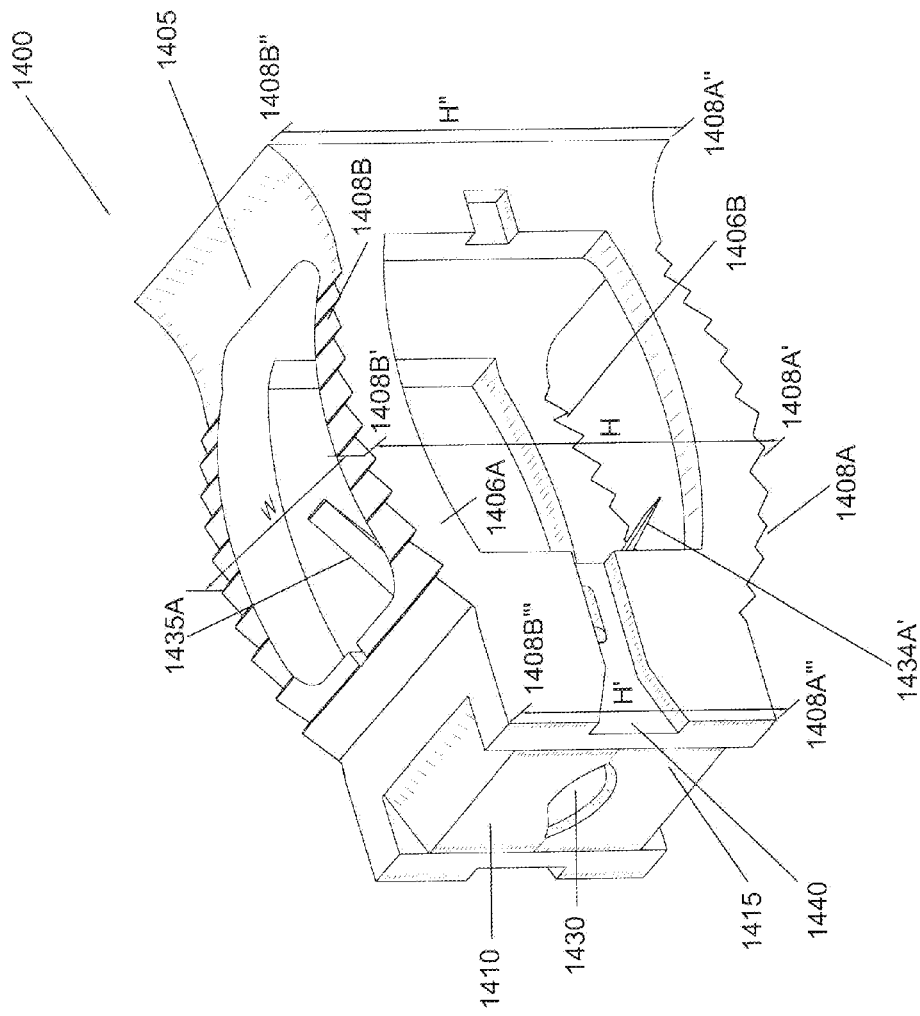

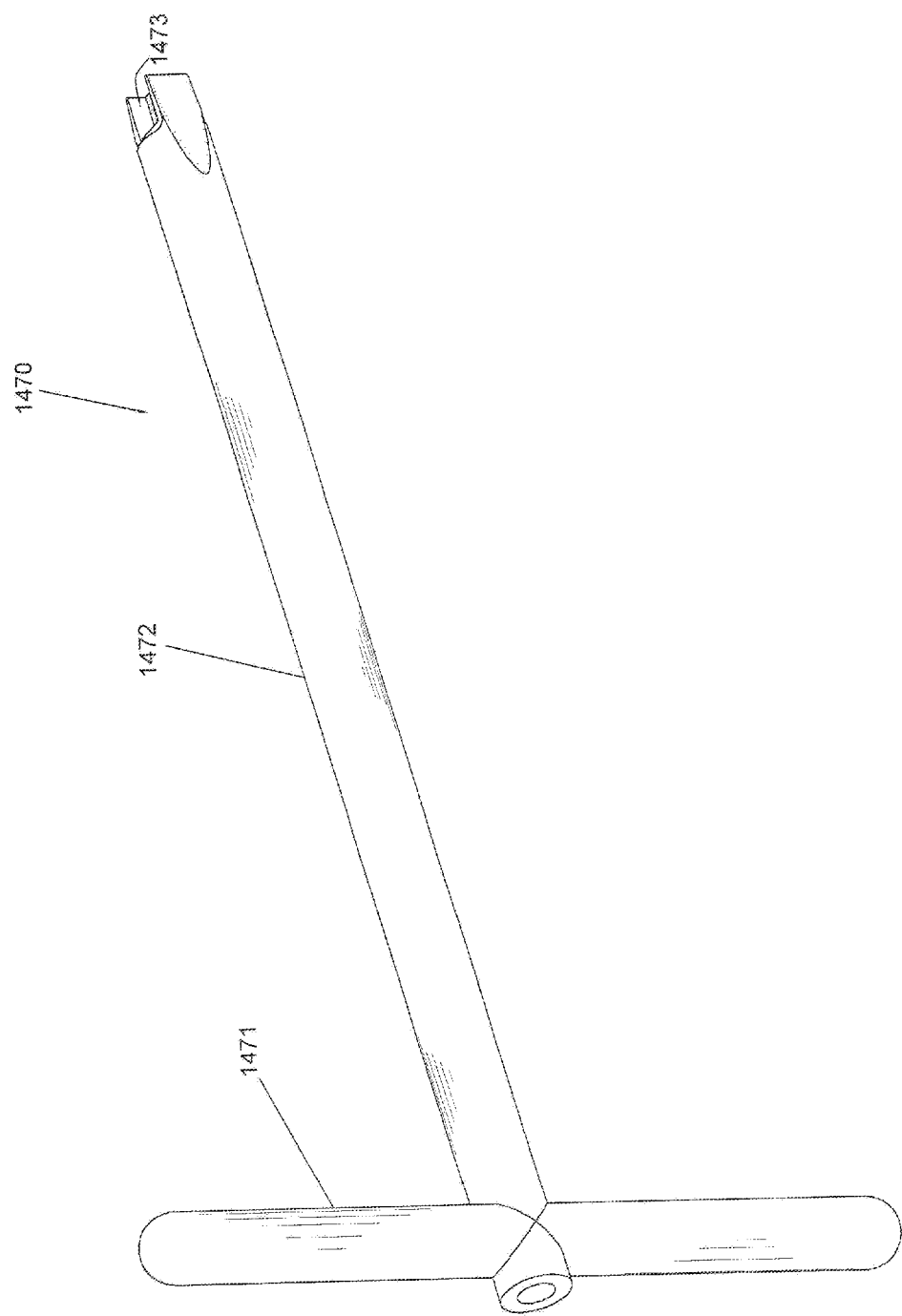

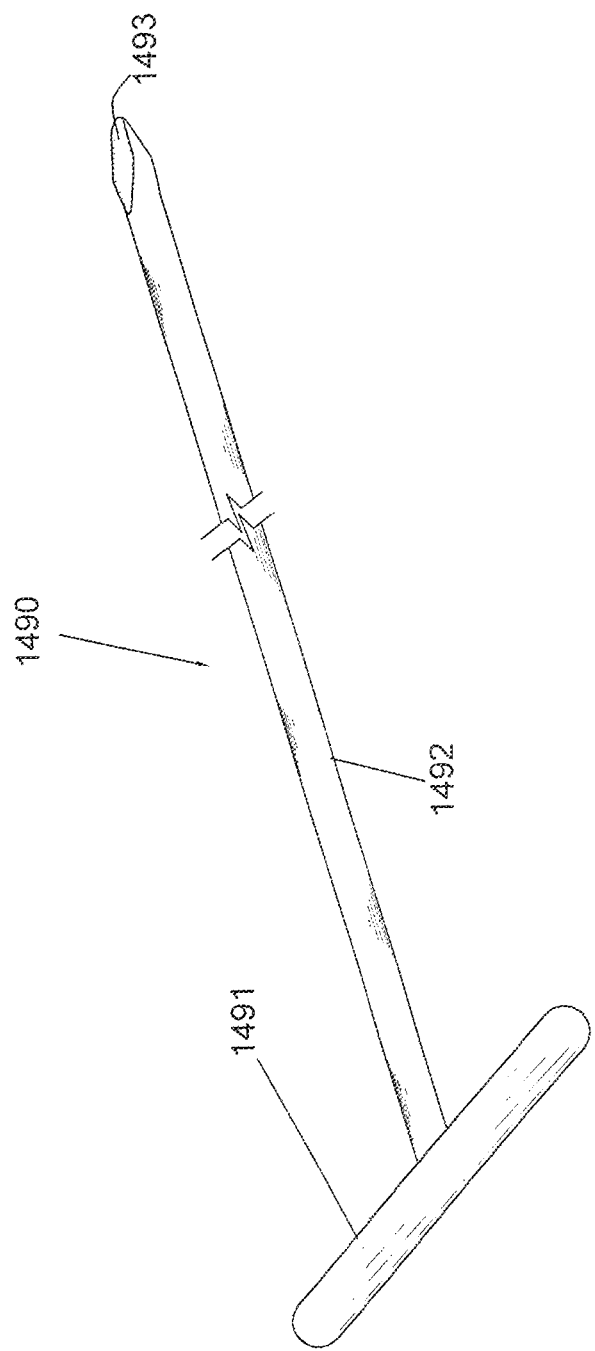

INTERVERTEBRAL DISK CAGE AND STABILIZER

FIELD OF THE INVENTION

The present invention relates to an intervertebral disk cage and stabilizer and a method of lumbar intervertebral disk stabilization with fusion.

SUMMARY OF THE INVENTION

There is a great need for standalone intervertebral disk cages that have inbuilt stabilizing means. This need is met by the one or more embodiments of the present invention. A method of stabilizing two adjacent vertebrae of a patient's spine after removal of a portion of the intervertebral disk to form a disk space there between includes providing an intervertebral disk implant. The implant comprises: (A) a biconvex cage, the cage comprising: a first pair of opposing sidewalls, wherein the first pair of sidewalls is substantially expanded in the middle, and wherein the first pair of sidewalls terminates in a flared tail portion; and an upper sidewall and a lower sidewall, wherein each of the upper sidewall, the lower sidewall and the first pair of sidewalls comprises an opening therewith to define an internal fenestrated channel, and (B) means for stabilizing the cage in an intervertebral disk space between a pair of adjacent vertebrae, wherein the stabilizing means substantially resists rotational movement of the biconvex cage. The implant can be inserted into the disk space of the patient so that the width dimension of the implant is parallel to the longitudinal axis of the patient's spine. The implant is rotated approximately 90 degrees in the disk space so that the height dimension is parallel to the longitudinal axis of the patient's spine. A means for stabilizing the cage is secured to the implant, wherein the stabilizing means has one or more surfaces for bearing against the body of the adjacent vertebrae to prevent rotation of the implant relative to the body of the adjacent vertebrae. An applicator can be mounted to one end of the cage before inserting the cage into the disk space. The cage can be rotated by rotating the applicator.

The stabilizing means can substantially reduce any migration of the cage. The stabilizing means can include one or more of a fish fin (flared tail) end portion on the cage; serrations on the surface of the cage sidewalls that are in contact with the surfaces of the intervertebral disks; an anchor nail; posterior slidable anchor plates; a posterior fixed pin; and a coating of porous or roughened titanium coating or a layer of calcium phosphate on the surface of the cage sidewalls that are in contact with the surfaces of the intervertebral disks. In one embodiment, the stabilizing means can include an anchor nail, wherein the anchor nail is received within an anchor nail slot located in a front end of the cage. The anchor nail further comprises: a substantially circular shaped central member, wherein the central member has a substantially hexagonal shaped internal slot; and first and second substantially rigid arms coupled to an outer surface of the central member. The first and second arms are configured to cut into an upper and lower vertebra respectively when the implant is positioned in the intervertebral disk space.

The stabilizing means can also include a pair of slidable anchor plates for cutting into the pair of adjacent vertebrae. The stabilizing means further comprises a pair of posterior end pins located substantially adjacent the slidable anchor plates, wherein the posterior end pins are configured to cut into the pair of adjacent vertebrae. In yet another embodiment, the stabilizing means further comprises a pair of hinged pins for cutting into the pair of adjacent vertebrae.

Also provided is a means for distracting the pair of slidable anchor plates, wherein the means for distracting the pair of slidable anchor plates is selected from a screw, a bolt or a nail. The means for distracting the pair of slidable anchor plates has a head having a diameter greater than the diameter of a cavity formed between the pair of slidable anchor plates such that the pair of slidable anchor plates is substantially prevented from moving back together.

In another embodiment, a connected intervertebral disk implant comprises: (A) first and second biconvex cages, each cage comprising: a first pair of opposing sidewalls, wherein the first pair of sidewalls is substantially expanded in the middle, and wherein the first pair of sidewalls terminates in a flared tail portion; and an upper sidewall and a lower sidewall, wherein each of the upper sidewall, the lower sidewall and the first pair of sidewalls comprises an opening therewith to define an internal fenestrated channel; (B) a connecting plate for coupling the first and second cages; and (C) means for stabilizing each of the first and second cages in an intervertebral disk space between a pair of adjacent vertebrae, wherein the stabilizing means substantially resists rotational movement of the biconvex cage.

Also provided is a kit consisting of the intervertebral disk implant and an applicator for detachably mounting to the cage, wherein the applicator has prongs formed thereon shaped to fit into slot formed on the cage.

BRIEF DESCRIPTION OF THE DRAWINGS

FIG. 1A is an exploded view of an intervertebral disk implant in an upright position in accordance with one embodiment of the invention.

FIG. 1B is an exploded view of an intervertebral disk implant in an upright position in accordance with another embodiment of the invention.

FIG. 2 is a perspective view of an initial position of the intervertebral disk implant when placed on the left side of the intervertebral disk space in accordance with one embodiment of the invention.

FIG. 4 is a view of a pair of anchor plates and anchor plate bolts in accordance with one embodiment of the invention.

FIG. 6 is a perspective view of the intervertebral disk implant with the anchor nail and anchor plates and anchor plate bolts in their final position in accordance with one embodiment of the invention.

FIG. 7 is a perspective view of an applicator for a bi-convex cage in accordance with one embodiment of the invention.

FIG. 8 is a perspective view of an applicator for an anchor nail in accordance with one embodiment of the invention.

FIG. 9 is a perspective view of an applicator for an anchor plate in accordance with one embodiment of the invention.

FIG. 10 is a perspective view of an applicator for an anchor plate bolt in accordance with one embodiment of the invention.

FIG. 11 is a perspective view of an integrated applicator for an anchor plate bolt and an anchor plate in accordance with one embodiment of the invention.

FIG. 12A is a lateral view of a portion of a human spinal column showing an initial position of an embodiment of the implant of the present invention inserted therein.

FIG. 12B is a lateral view of a portion of a human spinal column showing a final position of an embodiment of the implant of the present invention inserted therein.

FIG. 13B is a perspective view of the intervertebral disk implant rotated through ninety degrees in the intervertebral disk space in accordance with the second embodiment of the invention.

FIG. 13G is a perspective view of an applicator for the slidable anchor plates in accordance with the second embodiment of the invention.

FIG. 14B is a perspective view of the intervertebral disk implant rotated through ninety degrees in the intervertebral disk space in accordance with the third embodiment of the invention.

FIG. 14E is a perspective view of an applicator for an intervertebral disk cage in accordance with the third embodiment of the invention.

FIG. 14G is a perspective view of an applicator for the slidable anchor plates in accordance with the third embodiment of the invention.

DETAILED DESCRIPTION

Figure 3A:
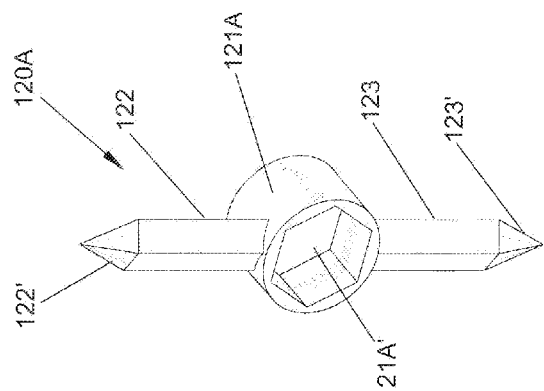
FIGS. 3A-3C are perspective views of an anchor nail in accordance with one embodiment of the invention.

The spine is a flexible structure comprised of thirty-three vertebrae separated and cushioned from each other by fibrous intervertebral disks except in the sacral and coccygial segments. If the spine is injured or becomes diseased, surgical intervention involving removal of one or more intervertebral disks and fusion of the adjacent vertebrae may be indicated. The more frequent injuries are those occurring in the lumbar and in the cervical regions.

Treatment of a herniated disk in the neck and the lumbar region continues to be a challenging field of medicine. The classical treatment for a ruptured disk continues to be diskectomy, that is, the removal of the intervertebral disk from between adjacent vertebrae. In this process, all or a portion of the intervertebral disk is removed, leaving a defect which continues to bother the patients throughout the rest of their lives. An additional procedure is to replace the intervertebral disk space with a bone graft, usually bone chips cut from the patient's iliac crest, bringing about fusion of the vertebrae above and below the intervertebral disk, eliminating the empty space between the adjacent vertebrae.

Theoretically, a diskectomy with fusion is a satisfactory procedure, however, it is not ideal because the replaced bone does not have any of the functions of the cartilaginous tissue of the intervertebral disk, that is, no cushioning effect, and has complications because of several factors. First, conventional bone plugs used to pack the intervertebral disk space do not conform to the shape of the disk because the disk bulges maximally in the center. The intervertebral disk space is wider in the middle and narrower at its anterior and posterior ends forming an overall biconvex shape. In the lumbar region this is further characterized by the lumbar lordosis which makes the anterior end of the disc space wider than posterior end. In the cervical region this difference is still there but very minimal. For this reason, the various bone plugs which are currently available commercially have only four contact points, i.e., at the front and back of the intervertebral disk space. Secondly, in the posterior lumbar procedures access to the intervertebral disk is from one side or the other of the dorsal spine of the adjacent vertebrae, leaving the bone plugs "off-center" relative to the bodies of the adjacent vertebrae. An implant inserted into that off-center space, therefore, replaces only a portion of the disk and consequently contacts only a portion of the bodies of the adjacent vertebrae such that the stability of the implant is even more problematic than might be apparent form the limited contact resulting from the shape of the intervertebral space in the first place. Also, if the bone pieces do not fuse, they may eventually extrude out of the intervertebral disk space, causing pressure on the nerve roots.

Various prosthetic disk plugs, or implants, are disclosed in the art, but all are characterized by limitations of not conforming to the shape of the intervertebral disk space, lack of stability when inserted off-center, inability to remove, or other disadvantages.

Accordingly, there is a need for a disk implant that can conform to the shape of the intervertebral disk space, provides lumbar intervertebral disk stabilization and promotes fusion through the disc space.

A novel method of providing lumbar intervertebral disk stabilization includes placing an intervertebral disk implant ("implant") in the intervertebral disk space between the bodies of two adjacent vertebrae in the disk space from which a portion of the intervertebral disk has been removed, i.e. by simple diskectomy and small laminectomy. The implant includes a rectangularly-shaped disk implant which is expanded in the middle portion. Also, disclosed are methods of lumbar intervertebral disk stabilization ("LIDS") with fusion.

In one embodiment, an intervertebral disk implant includes a cage and a stabilizer. The implant is preferably constructed of any durable, relatively biologically inert substance such as carbon fiber, titanium, several medical grade hard plastics, and such other materials as are known in the art for use in such implants.

Referring now to the figures, several exemplary embodiments of the present invention will be illustrated and described in further detail.

Exemplary First Embodiment

FIG. 1A shows an exemplary intervertebral disk implant 100A in accordance with a first embodiment. Implant 100A includes a cage 105A and a stabilizer 115A for securing the cage within the intervertebral disk space between two adjacent vertebrae. The stabilizer 115A includes an anchor nail 120A, anchor plate bolts 140A, 145A for securing the anchor nail to the anchor plates 130A, 135A for receiving anchor plate bolts 140A, 145A. FIG. 1A shows the desired or final position of the implant 100A when placed in the intervertebral disk space through a laminectomy approach from the left side.

FIG. 1B shows another exemplary intervertebral disk implant 100B. Implant 100B includes a cage 105B and a stabilizer 115B for securing the cage within the intervertebral disk space between two adjacent vertebrae. The stabilizer 115B includes an anchor nail 120B, anchor plate bolts 140B, 145B for securing the anchor nail to the anchor plates 130B, 135B for receiving anchor plate bolts 140B, 145B. FIG. 1B shows the final position of the implant 100B when placed in the intervertebral disk space through a laminectomy approach from the right side. While certain embodiments below are described only with reference to implant 100A (to be placed in the intervertebral disk space through a laminectomy approach from the left side), it should be obvious that the same would apply to implant 100B as well (to be placed in the intervertebral disk space through a laminectomy approach from the left side).

Referring now to FIG. 2, the implant 100A may be initially placed on the left side of the intervertebral disk space. The implant 100A includes cage 105A and stabilizer 115A. The cage 105A includes an upper sidewall 106A and a lower sidewall 106B. The cage 105A further includes two pairs of opposing sidewalls, posterior sidewall 107A, anterior sidewall 107B and 108A, 108B. Sidewall 107A may define a posterior sidewall end 107A' of the cage 105A while sidewall 107B may define an anterior sidewall end 107B' of the cage 105A. Sidewalls 108A, 108B can be substantially arched from the posterior sidewall end 107A' of the cage 105A to the anterior sidewall end 107B' of the cage 105A with an expanded portion in the middle. Accordingly, the cage 105A is substantially bi-convex. The middle expanded, bi-convex cage 105A increases the intervertebral disk height in the mid portion and facilitates stabilization of the intervertebral disk space to reduce anteroposterior migration. The surfaces of sidewalls 108A and 108B can also be serrated to further reduce the tendency to migration. The surfaces of sidewalls 108A and 108B can also be covered with a porous or roughened titanium coating and perhaps even a layer of calcium phosphate for this purpose; other suitable coatings/surfaces includes titanium wire mesh, plasma-sprayed titanium, porous cobalt-chromium and bio active materials such as hydroxyapatite and the aforementioned calcium phosphate. The surfaces of sidewalls 106A and 106B are flat anteroposteriorly.

Each of the sidewalls 106A, 106B, 108A and 108B can include an opening. The fenestrated channel 109A can be packed with cancellous bone chips as with prior known surgical methods. The fenestrated channel 109A can facilitate contact of the bone chips with the adjacent vertebrae above and below as well as bone chips in the disc space on either sides of the implant thereby facilitating bone fusion up and down and across the cage 105A in the intervertebral disk space.

The width "W" can be defined as the distance between sidewalls 106A and 106B. As will be explained below, the width W may be minimized to facilitate insertion and positioning of the implant 100A into the (left side) intervertebral disk space. The height H' of the implant 100A can be defined as the distance between 108A''' and 108B'''. The height will be different at the two ends 107A' and 107B' as well as in the middle of the implant due to the middle expanded design. Height H'' at 107B' will be longer than H' at 107A' when considering stabilization of disc space producing lumbar lordosis. H will be usually 5 mm more than H'. H'' can be same as H' or higher. The height H' determines the size of implant 100A that is utilized. In one or more embodiments, the width "W" of the implant 100A is 5 mm while the height H' of the implant 100A ranges from 8 mm to 16 mm. The height H' of the implant 100A may be greater than the width W. Height H'' (from 108A'' to 108B'') may be greater than the height H'.

Sidewalls 108A and 108B can terminate in a substantially flared tail portion 108A'' and 108B'' to resist anterior-posterior movement of the implant 100A in the intervertebral disk space. The flared tail portion can create a depression to prevent migration of the cage 105A when placed within the intervertebral disk space and also to auto correct itself within the intervertebral disk space. Since the surfaces of sidewalls 108A and 108B are serrated, the tendency for migration of the implant can be further reduced.

By making H''>H', with 5 and 10 degree sizes, the implant 100A can be custom fit into disk spaces with varying degrees of lordosis. Lordosis is mainly generated by the disk height being higher anteriorly compared to the posterior end of the disk. At the anterior end of the disk space, there is a noticeable expansion in the disk height. By incorporating the flared tail portion 108A'' and 108B'' and by making H''>H', this anatomical feature can be used to increase stabilization of the implant 100A.

The posterior sidewall end 107A' can be provided with an anchor nail slot 240A for receiving the anchor nail. The posterior sidewall end 107A' is further provided with at least a pair of bores 250A and 250B for receiving anchor plate bolts. The anchor plate bolts can be coupled to the anchor plates.

After implant 100A is placed in the intervertebral disk space (on the left side), implant 100A may be rotated ninety degrees in a counterclockwise direction so that it rests in the final position shown earlier in FIG. 1A. Sidewalls 108A, 108B provide the surfaces for bearing against the bodies of the adjacent vertebrae. Sidewalls 108A, 108B can be optionally provided with a plurality of teeth (serrated) for biting into the adjacent vertebrae to help resist anterior-posterior movement of the implant 100A in the disk space.

Figure 3B:
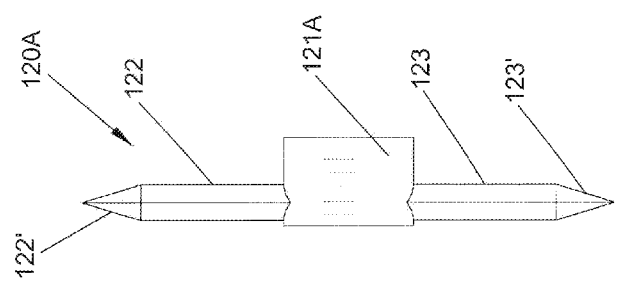
Figure 3C:
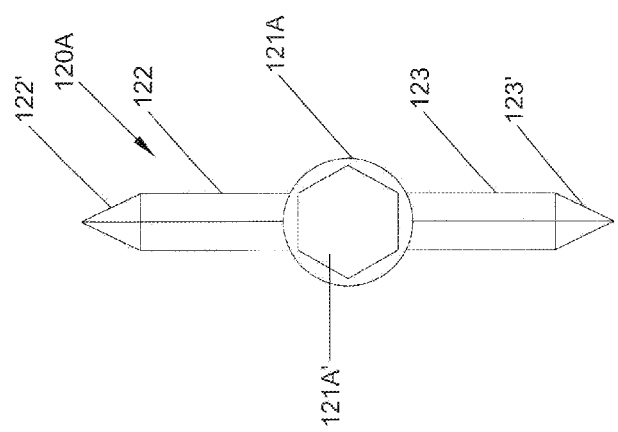

FIGS. 3A-3C depict a corner, side and front view of the anchor nail 120A according to one embodiment. The anchor nail 120A includes a central member 121A. The central member 121A can be substantially circular in shape. The central portion 121A can have an internal opening or slot that is substantially hexagonal in shape. A first arm 122A and a second arm 123A are coupled to the outer surface of the central member 121A. As used herein, the word "arm" includes a shaft or a substantially elongated member. The first arm 122A and the second arm 123A are substantially rigid. The ends of the first arm 122A' and the second arm 123A' can be substantially tapered to allow the anchor nail 120A to cut into the bone when rotated 90 degree clockwise. Referring back to FIG. 1A, the anchor nail 120A can cut into an upper and lower vertebra and prevent posterior migration of the implant 100A and keep the cage 105A in a locked configuration when the implant 100A is placed in the desired position in the intervertebral disk space.

FIG. 4 depicts an embodiment of the anchor plates 130A, 135A and anchor plate bolts 140A, 145A. The anchor plates 130A, 135A can include an anchor plate bolt opening 430A, 435A. In one embodiment, the anchor plate bolt openings 430A, 435A can be threaded internally (not shown). However, in a preferred embodiment, the anchor plate bolt openings 430A, 435A are not threaded. The anchor plate bolt openings 430A, 435A are dimensioned to receive anchor plate bolts 140A, 145A respectively. Anchor plate bolts 140A, 145A include a substantially rounded or spherical head 440A', 445A' and a threaded shank 442A, 447A coupled to the spherical heads 440A', 445A'. The threaded shanks 442A, 447A are configured to pass through anchor plate bolt openings 430A, 435A. The spherical heads 440A', 445A' can have a diameter that is larger than the anchor plate bolt openings 430A, 435A such that the anchor plate bolts 140A, 145A are held secureably in the openings 150A and 155A in FIG. 1.

Referring back to FIG. 1A, the implant 100A further includes openings 150A, 155A for the anchor plate bolts 140A, 145A. The openings 150A, 155A for the anchor plate bolts 140A, 145A are dimensioned to substantially overlap with the anchor plate bolt opening 430A, 435A on the anchor plates 130A, 135A. The openings 150A, 155A for the anchor plate bolts 140A, 145A can be threaded. The threaded shanks 442A, 447A of the anchor plate bolts 140A, 145A can fit into the complementary threads of the openings 150A, 155A for the anchor plate bolts 140A, 145A.

Figure 5A:
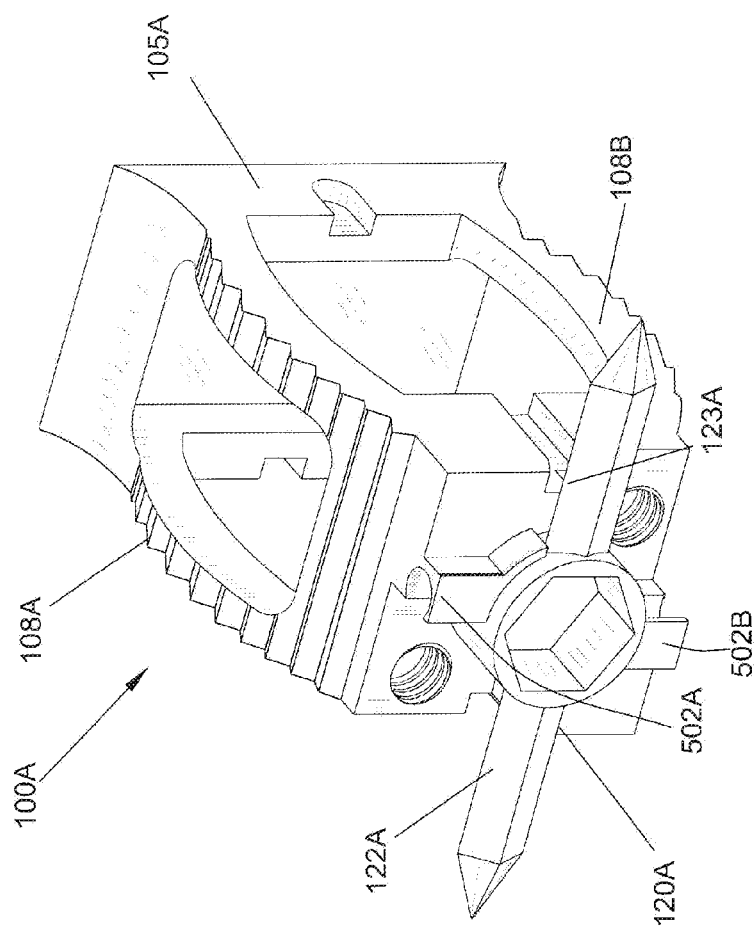
FIG. 5A is a view of the anchor nail positioned in an initial position in the intervertebral disk implant in accordance with one embodiment of the invention.
Figure 5B:
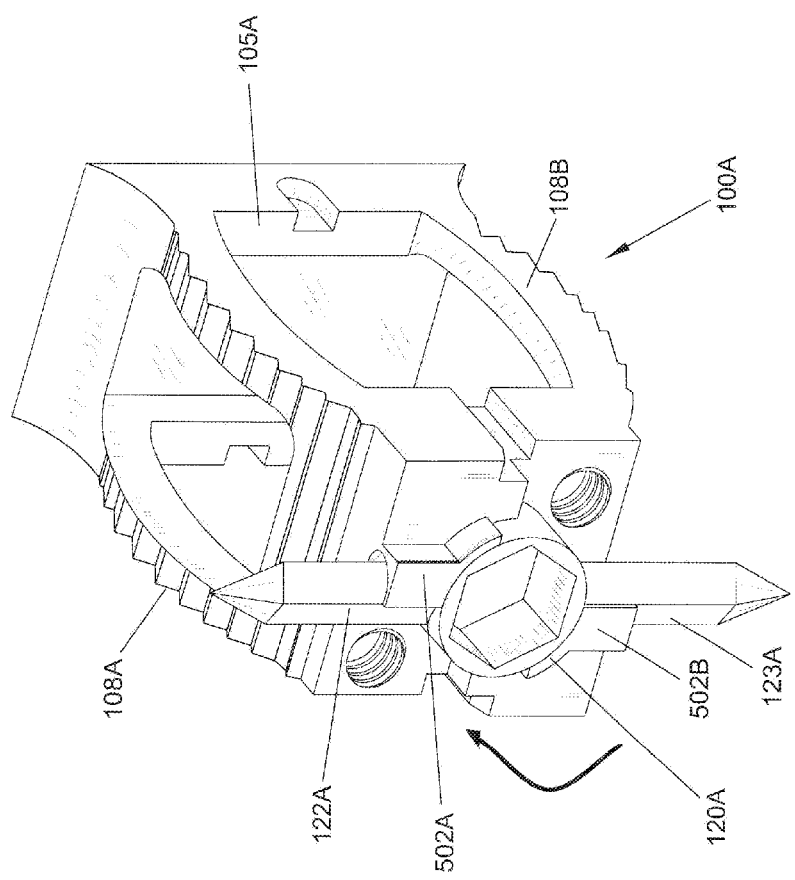
FIG. 5B is a perspective view of the anchor nail positioned in a final position in the intervertebral disk implant in accordance with one embodiment of the invention.

In another embodiment, a method of providing lumbar intervertebral disk stabilization includes placing the implant 100A in the intervertebral disk space between the bodies of two adjacent vertebrae in the disk space from which a portion of the intervertebral disk has been removed, i.e. by simple diskectomy and small laminectomy. As shown in FIG. 5A, the cage 105A is rotated and positioned in the desired configuration such that sidewalls 108A, 108B provide the surfaces for bearing against the bodies of an upper and a lower vertebra (not shown). The anchor nail 120A is positioned in the anchor nail slot such that the first arm 122A and the second arm 123A are parallel to the upper and lower vertebra and protrusions 502A, 502B. Now referring to FIG. 5B, the implant 100A includes a cage 105A. The cage 105A includes sidewalls 108A, 108B and a stabilizer comprising an anchor nail 120A. The anchor nail 120A is rotated ninety degrees in a clockwise direction such that the first arm 122A and the second arm 123A cut into the upper and the lower vertebra respectively. The first arm and second arm 122A, 123A can be securely held in position within grooves formed in protrusions 502A, 502B.

FIG. 6 shows an embodiment of the implant 100A comprising a bi-convex cage 105A and a stabilizer 115A with the anchor nail 120A positioned in the anchor nail slot and rotated clockwise such that the first arm 122A and 123A cut into an upper and a lower vertebra. Anchor plate bolts 140A, 145A are connected to the anchor plates 130A and 135A respectively and screwed into place.

FIG. 7 depicts an exemplary cage applicator 700 for the implant 100A. The applicator 700 comprises an elongate shaft 710 and a handle 720 at a first end of the shaft 710. The handle 720 can be "T" shaped. However, it will be recognized from this disclosure by those skilled in the art that the handle 720 may take the form of any convenient hand grip or other structure which facilitates the handling of the implant 100A. A second end of the shaft 710 can include two prongs 730A and 730B. Keys 740A and 740B are formed on an inner surface of prongs 730A and 730B. The keys 740A and 740B can be raised protrusions that can be dimensioned to fit within a complementary lock or groove formed on the implant 100A.

FIG. 8 shows an exemplary anchor nail applicator 800 for the anchor nail 120A. The applicator 800 comprises an elongate shaft 810 and a handle 820 at a first end of the shaft 810. The handle 820 can be "T" shaped. However, it will be recognized from this disclosure by those skilled in the art that the handle 820 may take the form of any convenient hand grip or other structure. The second end of the shaft 810 terminates in a substantially hexagonal shaped inserter 830. The hexagonal shaped inserter 830 is dimensioned to fit within the hexagonal shaped internal slot of the anchor nail 120A.

FIG. 9 shows an exemplary anchor plate applicator 900 for anchor plates 130A (shown) and 135A (not shown). The applicator 900 includes an elongate shaft 910 and a handle 920 at a first end of the shaft 910. The handle 920 is in the shape of a "T", but it will be recognized from this disclosure by those skilled in the art that the handle 920 may take the form of any convenient hand grip or other structure which facilitates the handling of the anchor plate applicator. The second end of the shaft 910 has an anchor plate socket 930 to hold the anchor plate 130A.

FIG. 10 shows an exemplary anchor plate bolt applicator 1000 for the anchor plate bolt 140A and 145A (not shown). The applicator 1000 includes an elongate shaft 1010 and a handle 1020 at a first end of the shaft 1010. The handle 1020 is in the shape of a "T", but it will be recognized from this disclosure by those skilled in the art that the handle 1020 may take the form of any convenient hand grip or other structure which facilitates the handling of the anchor plate bolt 140A, and subsequent rotation of the anchor plate bolt 140A once it has been inserted through the anchor plate and into 150A or 155A on implant 100A in FIG. 1. In addition, the applicator 1000 for the anchor plate bolt has a set screw hex 930 at the second end of the shaft 1010 for coupling to the anchor plate bolt 140A.

FIG. 11 shows an exemplary integrated applicator 1100 for the anchor plate bolt 140A and the anchor plate 130A. The applicator 1100 includes an elongate shaft 1110 and handles 1120 and 1125 at a first end of the shaft 1110. The handles 1120 and 1125 are in the shape of a "T", but it will be recognized from this disclosure by those skilled in the art that the handles 1120 and 1125 may take the form of any convenient hand grip or other structure which facilitates the handling of the anchor plate bolt 140A and the anchor plate 130A, and subsequent rotation of the anchor plate bolt 140A once it has been inserted through the anchor plate 130A into 150A and 155A on 100A. The applicator 1100 has a set screw hex 1140 at the second end of the shaft 1110 for coupling to the anchor plate bolt 140A and an anchor plate holder 1130 for the anchor plate 130A.

In another embodiment, as illustrated in FIGS. 12A and 12B, a method of lumbar intervertebral disk stabilization, or "LIDS," can be performed using implant 100A. For example surgery is performed as in a simple diskectomy and the intervertebral disk 18 is exposed through a small laminectomy on the left side. The disk material is removed and any nerve root compression is corrected. The disk cartilages are removed until the surface of the bodies 10 and 12 of adjacent vertebrae 14 and 16, respectively, are exposed above and below the disk space.

Using spreaders known in the art, the vertebrae 14 and 16 are distracted to open the disk space. Once the desired "spread" is achieved, the middle portion of the disk space and the opposite sides are packed with cancellous bone chips (not shown). Because the posterior longitudinal ligament is left intact to the opposite side and to the center of the disk space, the bone chips are held in place in the disk space.

The cage 105A can be placed on the left side and rotated ninety degrees counterclockwise in the intervertebral disk space using an appropriate cage applicator (as described earlier). As shown in FIG. 12B, this causes the sidewalls 108A, 108B to bear against the bodies 10 and 12 and move the implant 100A further into (or back out of, depending upon the direction of rotation) the disk space to the right so as to enable the cage 105A to be positioned in the intervertebral disk space at a position in which the expanded middle portion contacts the respective lower and upper surfaces of the adjacent vertebrae 14 and 16. The respective lower and upper surfaces of the vertebral bodies 14 and 16 are slightly concave such that the expanded middle portion of cage 105A allows the cage 105A to engage substantially more of the respective surfaces of the vertebral bodies 14 and 16 than conventional prosthetic devices, thereby providing increased stability to the implant and better prospect for bone fusion.

Once the cage 105A is positioned in the intervertebral disk space so as to provide maximum stabilization, the cage applicator may be detached from the cage 105A by backing out of the incision in the patient.

The anchor nail 120A is then inserted into the anchor nail slot 240A using an appropriate anchor nail applicator (as described earlier) until anchor nail 120A is properly positioned in the anchor nail slot. The anchor nail 120A is then rotated ninety degrees clockwise while in the anchor nail slot using the anchor nail applicator. Once the anchor nail 120A is positioned on the cage 105A and its arms cut in to the vertebral end plates, the anchor nail applicator is detached from the anchor nail 120A by pulling it out from the hexagonal slot of the anchor nail 120A and backed out of the incision in the patient.

The anchor plates (as described earlier) can be inserted onto the cage 105A using an appropriate anchor plate applicator (as described earlier). Once the anchor plates are positioned on the cage 105A, an anchor plate bolt applicator with anchor plate bolt attached at its hexagonal end can be inserted through the hollow cylindrical channel in the anchor plate applicator and the anchor plate bolt can be screwed into the threads on the cage 105A via the anchor plate bolt openings. Followed by that the anchor plate applicator together with anchor plate bolt applicator can be detached from the anchor plate, and backed out of the incision in the patient.

The fenestrated channel within the cage can be packed with cancellous bone chips as with prior known surgical methods. If necessary, a small amount of a physiologically compatible adhesive of a type known in the art is applied over the cancellous bone chips just medial to the implant to close off the remaining portion of the opening into the disk space.

While rotating the cage 105A in the counterclockwise direction, the top right and bottom left portions of the vertebral body in relation to the cage 105A may be weakened. The anchor plates can, therefore, be placed in the top left and bottom right portions where the bone is not weakened by the rotation of the cage 105A. This position of the anchor plates may also help to prevent the anchor nail 120A from rotating it back to its initial position.

Removal of the implant 100A can be accomplished with relative ease compared to conventional implants. The anchor plate bolt applicator can be used to unscrew the anchor plate bolts connected to the anchor plates and are thus removed from the cage 105A and from the intervertebral disk space. The anchor plate applicator can be used to remove the anchor plates and are thus removed from the cage 105A and from the intervertebral space as well.

The anchor nail applicator can be reattached to the anchor nail 120A and the anchor nail 120A rotated ninety degrees counterclockwise to remove the anchor nail 120A from the anchor nail slot on the cage 105A and from the intervertebral disk space. Finally, the cage applicator 105A is reattached to the cage 105A and the cage 105A rotated ninety degrees clockwise to remove the cage 105A from the intervertebral disk space.

Exemplary Second Embodiment

Figure 13A:
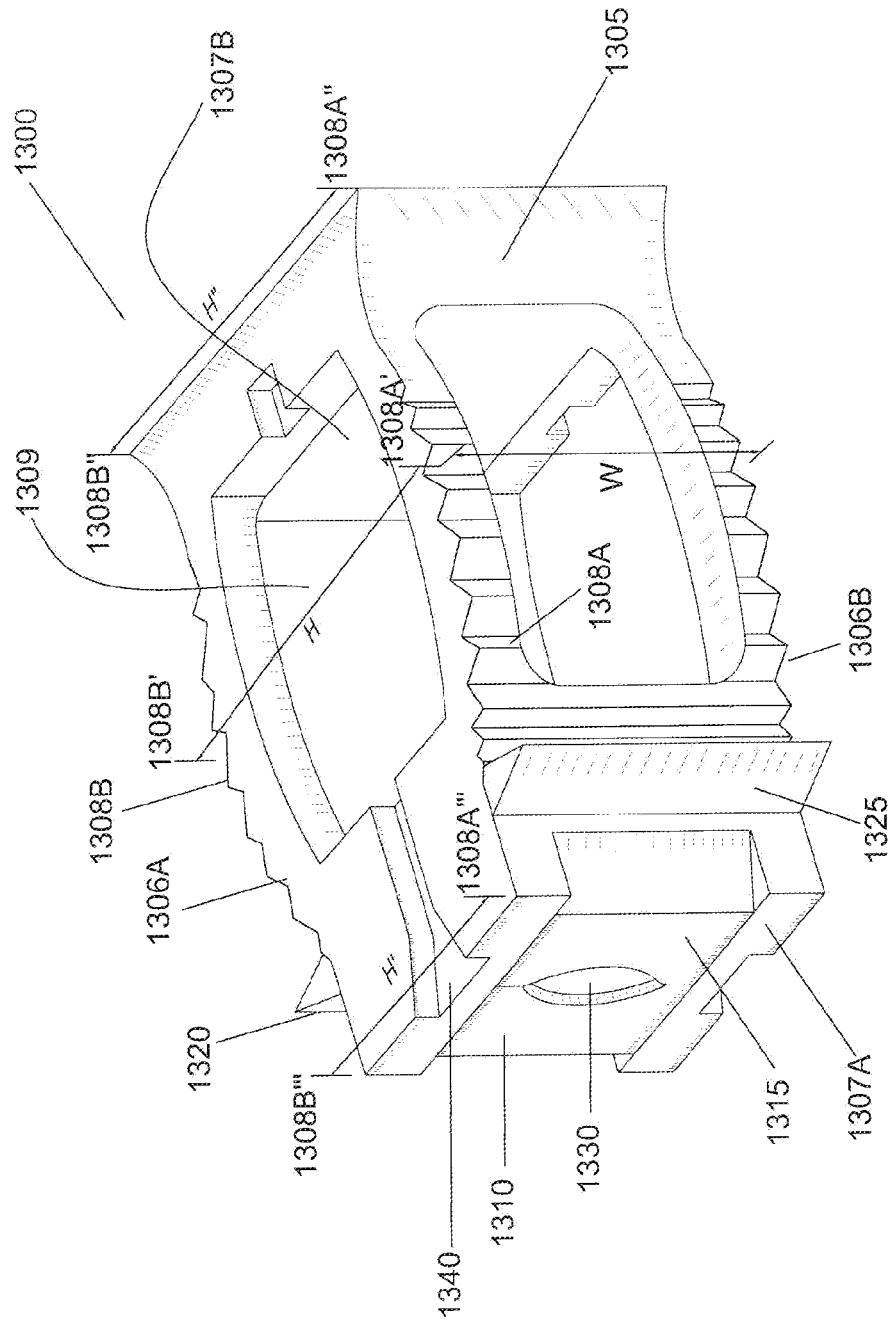
FIG. 13A is a perspective view of an initial position of the intervertebral disk implant when placed in the intervertebral disk space in accordance with a second embodiment of the invention.
Figure 13C:
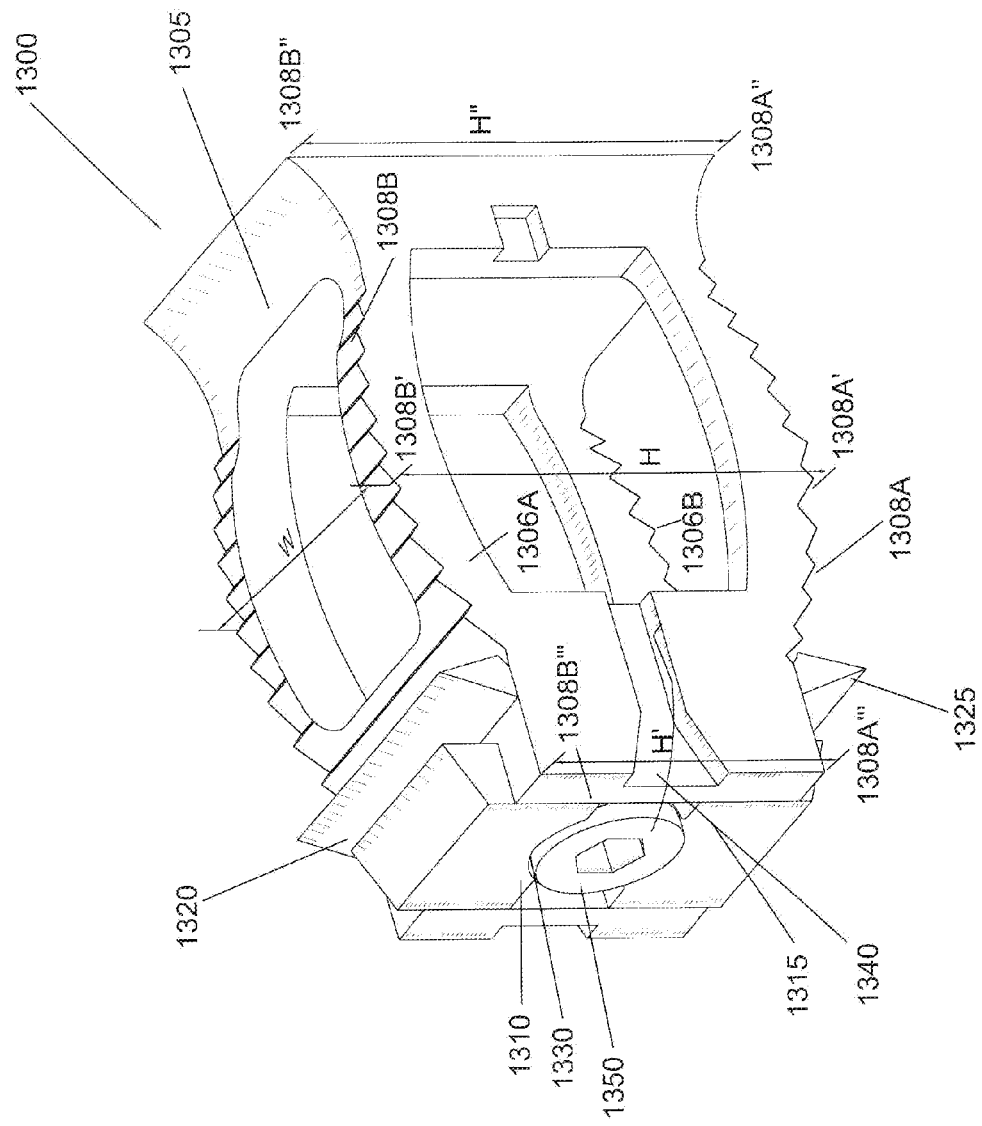
FIG. 13C is a perspective view of the intervertebral disk implant in its final position in accordance with the second embodiment of the invention.

FIGS. 13A, 13B and 13C illustrate a second embodiment 1300 of an intervertebral disk implant. The second embodiment of the implant 1300 includes a unilateral or self-standing cage with a plurality of built-in features that facilitate stabilization of the implant 1300 when it is placed in the intervertebral disk space. The implant 1300 includes cage 1305. The cage 1305 includes an upper sidewall 1306A and a lower sidewall 1306B. The cage 1305 further includes opposing sidewalls 1308A and 1308B. Sidewalls 1308A, 1308B can be substantially arched from one end of the cage 1305 to a second end of the cage 1305 with an expanded portion in the middle. Accordingly, the cage 1305 is substantially bi-convex. The middle expanded, bi-convex cage 1305 increases the intervertebral disk height and facilitates stabilization of the intervertebral disk space and promotes bone fusion.

Each of the sidewalls 1306A, 1306B, 1308A and 1308B can include an opening. The openings define an internal fenestrated channel 1309 within the cage 1305. The fenestrated channel 1309 can be packed with cancellous bone chips as with prior known surgical methods. The fenestrated channel 1309 can facilitate contact of the bone chips with the adjacent vertebrae thereby facilitating bone fusion across the cage 1305, up and down and also with the bone chips outside the cage 1305 in the intervertebral disk space on either side.

The width "W" can be defined as the distance between sidewalls 1306A and 1306B. As will be explained below, the width W may be minimized to facilitate insertion and positioning of the implant 1300 into the intervertebral disk space. The height H' of the implant 1300 can be defined as the distance between 1308A' and 1308B' at the posterior sidewall end of the implant. The height H' determines the size of implant 1300 that is utilized. The height H' of the implant 1300 may be greater than the width W. H can be greater than H" and H' and H" can be greater than H'.

Sidewalls 1308A and 1308B can terminate in a substantially flared tail portion adjacent sidewall 1307B to resist anterior-posterior movement of the implant 1300 in the intervertebral disk space. The flared tail portion can include a depression to prevent migration of the cage 1305 when placed within the intervertebral disk space and to auto correct itself within the intervertebral disk space in flexion and extension.

In one embodiment, the surfaces of sidewalls 1308A and 1308B can also be serrated to further reduce the tendency to migration. The surfaces of sidewalls 1308A and 1308B can also be covered with a porous or roughened titanium coating and perhaps even a layer of calcium phosphate for this purpose; other suitable coatings/surfaces includes titanium wire mesh, plasma-sprayed titanium, porous cobalt-chromium and bio active materials such as hydroxyapatite and the aforementioned calcium phosphate. The surfaces of sidewalls 1306A and 1306B can be flat anteroposteriorly.

By making H">H', with 5 and 10 degree sizes, the implant 1300 can be custom fit into disk spaces with varying degrees of lordosis. Lordosis is mainly generated by the disk height being higher anteriorly compared to the posterior end of the disk. At the anterior end of the disk space, there is a noticeable expansion in the disk height. By incorporating the flared tail portion, this anatomical feature can be used to increase stabilization of the implant 1300. The flared tail portion also facilitates to cut past the surfaces of adjacent vertebrae in the intervertebral disk cavity. The flared tail portion can include a depression to prevent migration of the cage 1305 when placed within the intervertebral disk space and to auto correct itself with the intervertebral disk space.

The inner surface of sidewall 1307A can include a pair of opposing channels (not shown) for secureably receiving a pair of slidable anchor plates 1310, 1315. A first end of the slidable anchor plates 1310, 1315 can include a beveled edge to facilitate cutting into the surfaces of adjacent vertebrae in the intervertebral disk cavity. A second end of each slidable anchor plates 1310, 1315 can include a semi-circular notch such that when the slidable anchor plates 1310, 1315 mate and substantially completely reside within the cage 1305, a cavity 1330 is defined between slidable anchor plates 1310 and 1315. The cage 1305 further includes a pair of posterior fixed pins 1320, 1325. The posterior fixed pins 1320, 1325 can be positioned on an outer surface of sidewalls 1308A, 1308B substantially adjacent sidewall 1307A. The cage 1305 further includes a track 1340 for receiving an applicator.

In one embodiment, a method of performing LIDS includes placing the cage 1305 horizontally (as shown in FIG. 13A) between the surfaces of adjacent vertebrae in the intervertebral disk cavity. The cage 1305 is then rotated through 90 degrees (as shown in FIG. 13B) to a vertical position using an appropriate applicator. The applicator can be placed in track 1340.

Now referring to FIG. 13C, a self locking screw 1350 is inserted into the cavity 1330 formed between the slidable anchor plates 1310, 1315 using an appropriate applicator. The head of the self locking screw 1350 can be shaped appropriately, for example, it can be conical to push the slidable anchor plates 1310, 1315 apart. The self locking screw 1350 is dimensioned such that it has greater dimension than cavity 1330 such that it is locked securely in the cavity 1330 thereby preventing the slidable anchor plates 1310, 1315 from coming back together. The self locking screw 1350 includes a threaded portion on its head which can cut into the semi-circular notches of the slidable anchor plates 1310, 1315 and can be locked in position thereby preventing the self locking screw 1350 from coming out of the cavity. When the self locking screw 1350 is turned the slidable anchor plates 1310, 1315 can be distracted upwards and downwards respectively through the channel provided in the cage 1305. The slidable anchor plates 1310, 1315 can be configured to stop further movement upon reaching an end of a slot in the sliding path. This causes the beveled ends of the slidable anchor plates 1310, 1315 to cut into an upper and a lower vertebra in the intervertebral disk space. The beveled ends of posterior fixed pins 1320, 1325 also cut into the upper and lower vertebra in the intervertebral disk space thereby providing further stabilization to the cage 1305 by substantially resisting the migration of the implant 1300 in the intervertebral disk space.

Figure 13D:
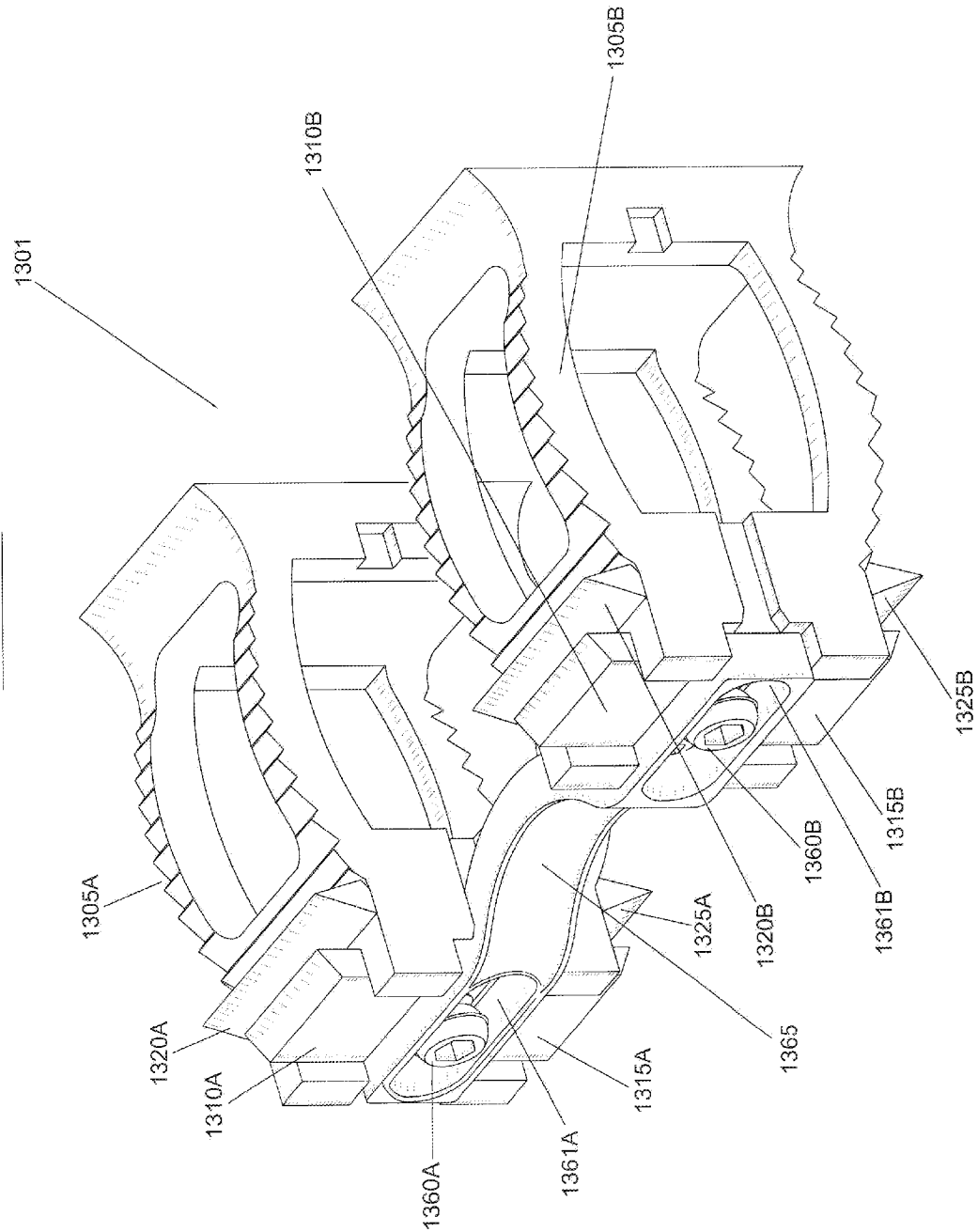
FIG. 13D is a perspective view of a connected intervertebral disk implant in its final position in accordance with a modified second embodiment of the invention.

FIG. 13D shows an exemplary embodiment of a connected implant 1301. The connected implant 1301 includes a pair of cages 1305A, 1305B. Cages 1305A, 1305B are substantially similar to cage 1300 described earlier. However, cages 1305A, 1305B differ from cage 1305 in that they are not independent. A connecting plate 1365 connects cages 1305A, 1305B which thereby causes them to act as a single interdependent unit. The self locking screws 1360A, 1360B can get locked in the connecting plate 1365 as opposed to between the slidable anchor plates 1310, 1315 in the case of cage 1305. Also, while one end of sliding plates 1310A, 1315A and 1310B, 1315B may terminate in a beveled edge, a second end may be substantially planar (and may be devoid of a semi-circular notch as in the case of sliding plates 1310, 1315).

In one embodiment, a method of performing LIDS includes placing cages 1305A, 1305B horizontally (not shown) between the surfaces of adjacent vertebrae in the intervertebral disk cavity. The cages 1305A, 1305B are then rotated through 90 degrees (as shown in FIG. 13D) to a vertical position using an appropriate applicator. As described with reference to FIG. 13C, the flared tail portion can cut past the bone in the intervertebral disk space. Using a device such as a screw driver, the slidable anchor plates 1310A, 1315A and 1310B, 1315B can be distracted upwards and downwards through a channel provided in the cages 1305A, 1305B. Connecting plate 1365 is placed into a slot (not shown) in the cages 1305A, 1305B such that slidable anchor plates 1310A, 1315A and 1310B, 1315B can be kept in a distracted position. The connecting plate 1365 can be provided with a curvature to accommodate the dural sac. After the connecting plate 1365 is positioned, screws 1360A, 1360B are inserted into openings 1361A, 1361B in the connecting plate 1365 such that they are locked in position. The openings also 1361A, 1361B in the connecting plate 1365 facilitate a desired intercage distance during surgery. The beveled ends of posterior fixed pins 1320A, 1325A and 1320B, 1325B also cut into the upper and lower vertebra in the intervertebral disk space thereby providing further stabilization to the cage 1305A, 1305B by substantially resisting the migration of the implant 1301 in the intervertebral disk space. Stabilization can also be accomplished by other methods available in the market. One such example includes the fixation of adjacent vertebra with pedicle screws and plates/rods.

Figure 13E:
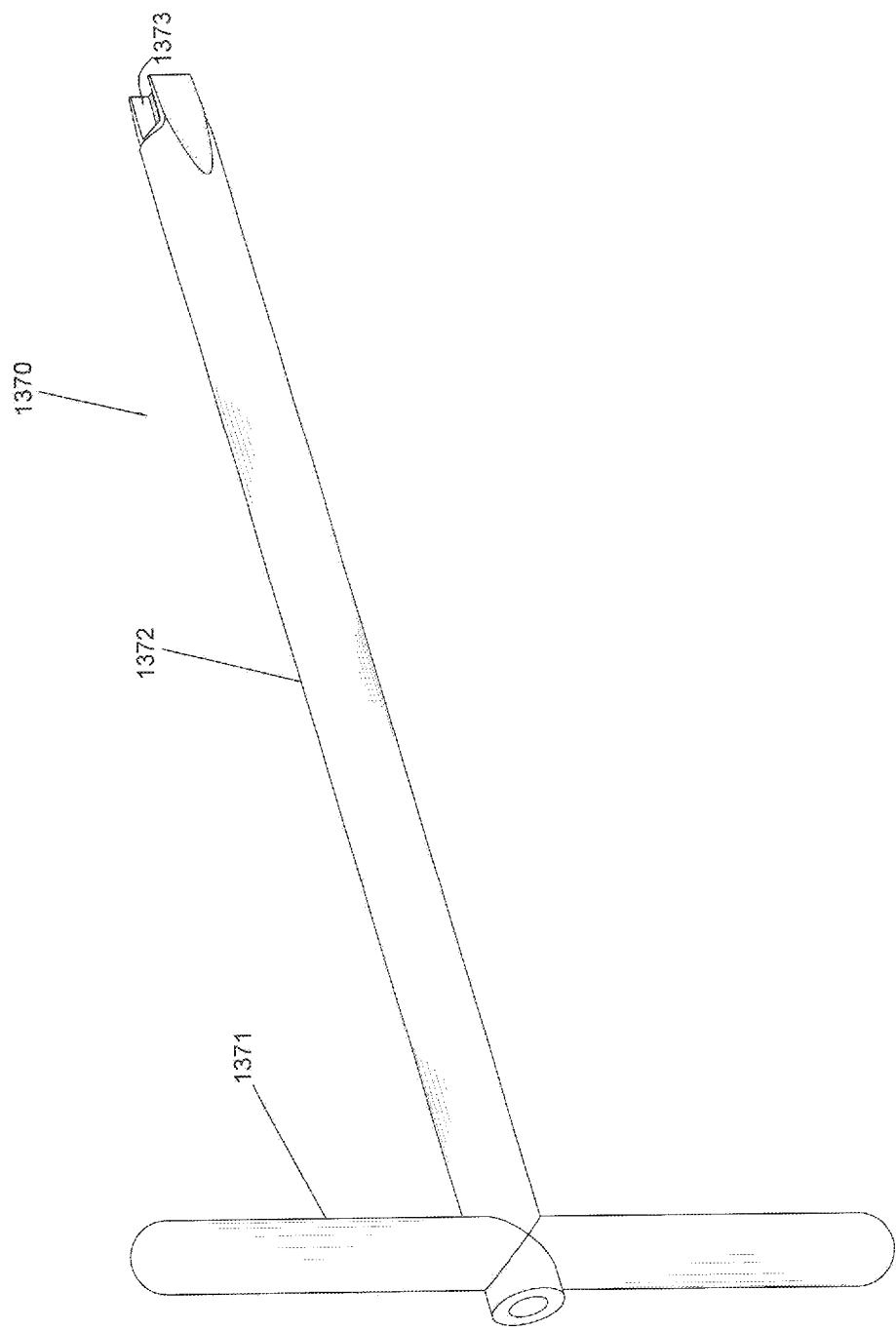
FIG. 13E is a perspective view of an applicator for an intervertebral disk cage in accordance with the second embodiment of the invention.
Figure 13F:
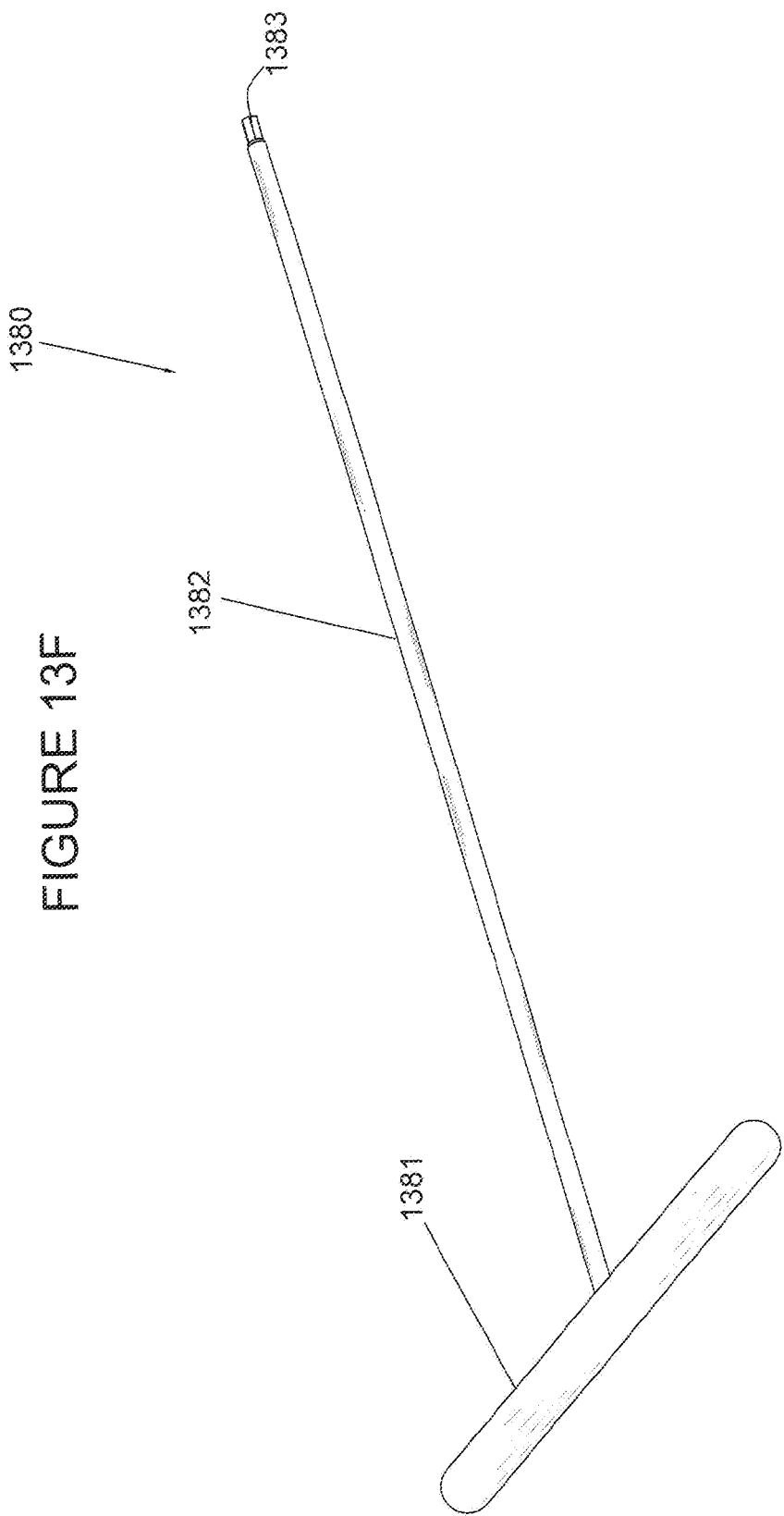
FIG. 13F is a perspective view of an applicator for the self locking screw in accordance with the second embodiment of the invention.

FIG. 13E shows an exemplary embodiment of an applicator 1370 for the cage 1305. FIG. 13F shows an exemplary embodiment of an applicator 1380 for the self locking screw 1350. FIG. 13G shows an exemplary embodiment of an applicator 1390 for the slidable anchor plates 1310, 1315. Each applicator 1370, 1380, 1395 includes a handle 1371, 1381, 1391 respectively. The handles 1371, 1381, 1391 can be coupled to an elongated shaft 1372, 1382, 1392 respectively. Each shaft 1372, 1382, 1392 terminates in a tip 1373, 1383, 1393 respectively. The tips 1373, 1383, 1393 can be shaped and dimensioned to receive the cage 1305, self locking screw 1350 and the slidable anchor plates 1310, 1315.

Exemplary Third Embodiment

Figure 14A:
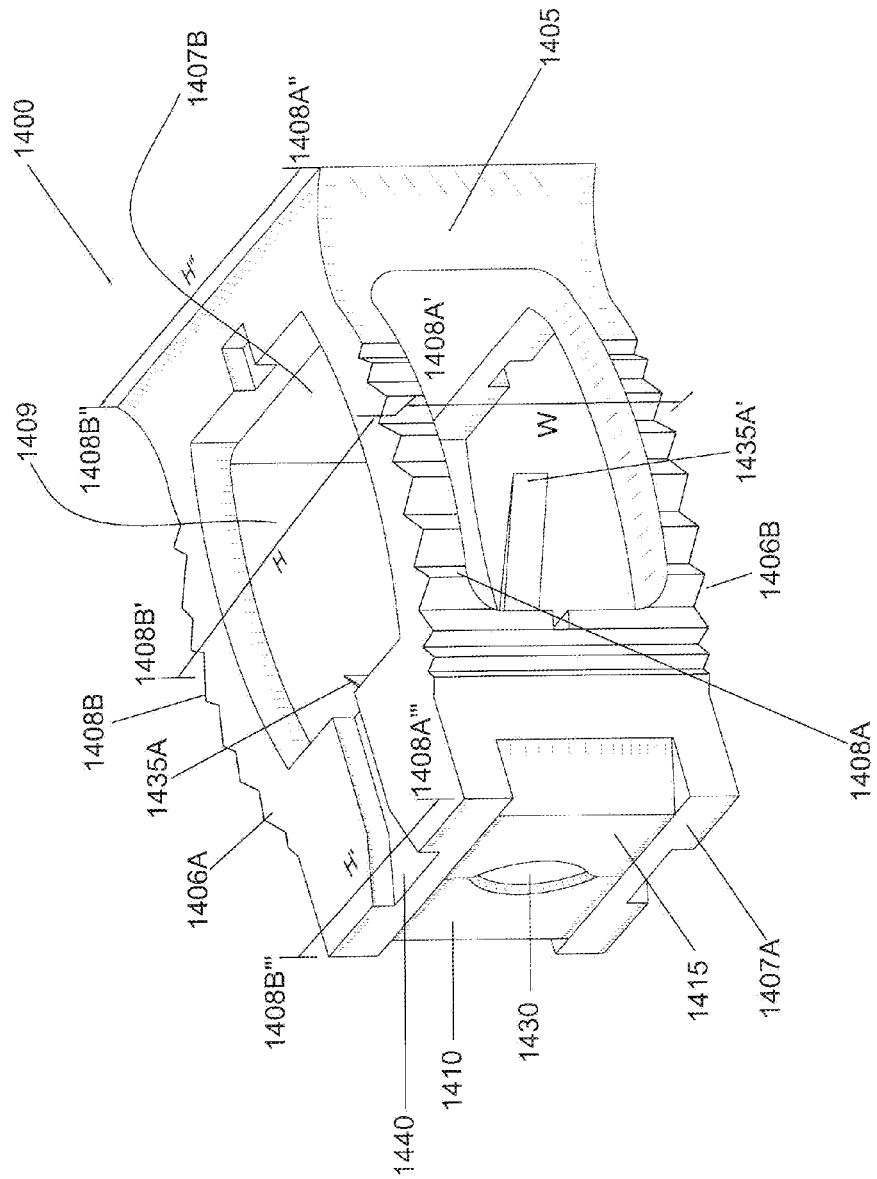
FIG. 14A is a perspective view of an initial position of the intervertebral disk implant when placed in the intervertebral disk space in accordance with a third embodiment of the invention.
Figure 14C:
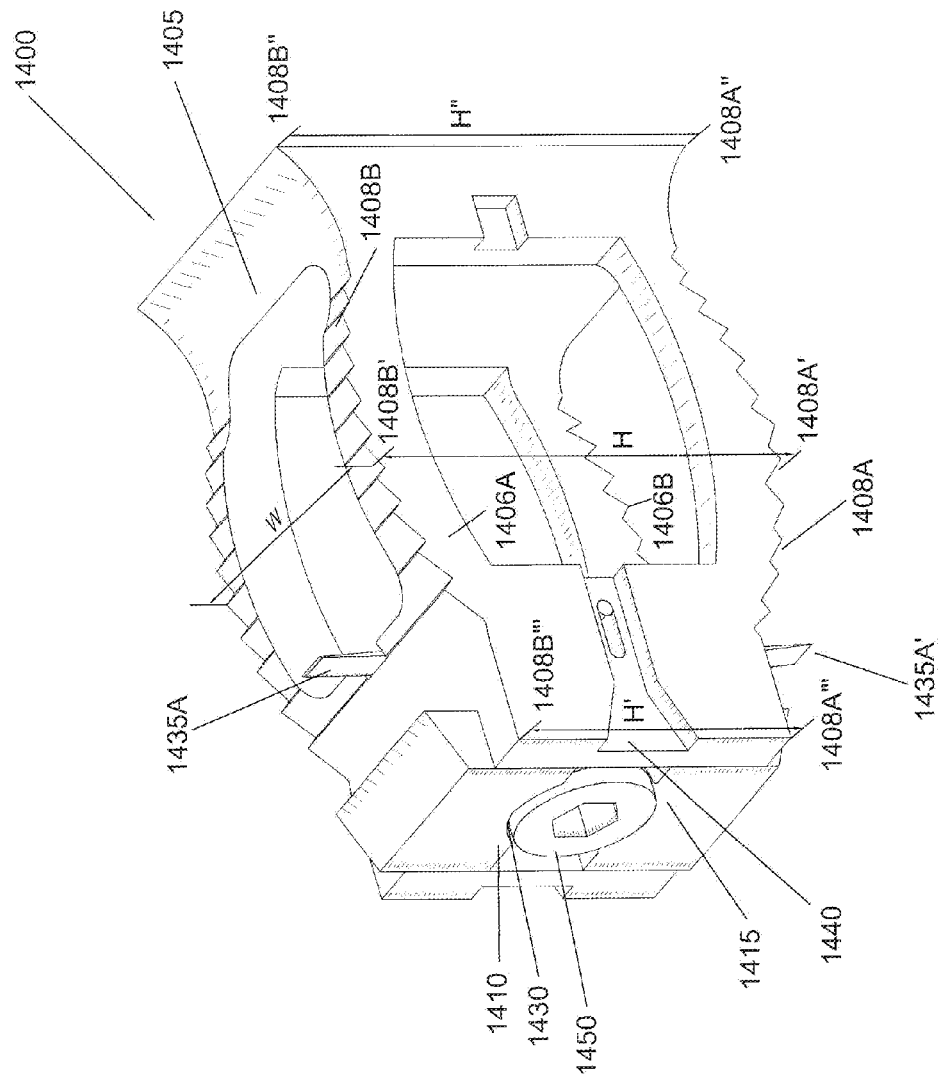
FIG. 14C is a perspective view of the intervertebral disk implant in its final position in accordance with the third embodiment of the invention.

FIGS. 14A, 14B and 14C illustrate a second embodiment 1400 of an intervertebral disk implant. The third embodiment of the implant 1400 includes a unilateral or self-standing cage with a plurality of built-in features that facilitate stabilization of the implant 1400 when it is placed in the intervertebral disk space. The implant 1400 includes cage 1405. The cage 1405 includes an upper sidewall 1406A and a lower sidewall 1406B. The cage 1405 further includes opposing sidewalls 1408A and 1408B. Sidewalls 1408A, 1408B can be substantially arched from one end of the cage 1405 to a second end of the cage 1405 with an expanded portion in the middle. Accordingly, the cage 1405 is substantially bi-convex. The middle expanded, bi-convex cage 1405 increases the intervertebral disk height and facilitates stabilization of the intervertebral disk space.

Each of the sidewalls 1406A, 1406B, 1408A and 1408B can include an opening. The openings define an internal fenestrated channel 1409 within the cage 1405. The fenestrated channel 1409 can be packed with cancellous bone chips as with prior known surgical methods. The fenestrated channel 1409 can facilitate contact of the bone chips with the adjacent vertebrae thereby facilitating bone fusion across the cage 1405, up and down and also with the bone chips outside the cage 1405 in the intervertebral disk space on either side.

The width "W" can be defined as the distance between sidewalls 1406A and 1406B. As will be explained below, the width W may be minimized to facilitate insertion and positioning of the implant 1400 into the intervertebral disk space.

The height "H" of the implant 1400 can be defined as the distance between 1408A' and 1408B' at the posterior sidewall end. The height H' determines the size of implant 1400 that is utilized. The height H' of the implant 1400 may be greater than the width W. Height H' and H" may be lesser than the height H. Furthermore, H' may be less than H".

Sidewalls 1408A and 1408B can terminate in a substantially flared tail portion adjacent sidewall 1407B to resist anterior-posterior movement of the implant 1400 in the intervertebral disk space.

In one embodiment, the surfaces of sidewalls 1408A and 1408B can also be serrated to further reduce the tendency to migration (not shown). The surfaces of sidewalls 1408A and 1408B can also be covered with a porous or roughened titanium coating and perhaps even a layer of calcium phosphate for this purpose; other suitable coatings/surfaces includes titanium wire mesh, plasma-sprayed titanium, porous cobalt-chromium and bio active materials such as hydroxyapatite and the aforementioned calcium phosphate. The surfaces of sidewalls 1406A and 1406B can be flat anteroposteriorly.

By making H">H', with 5 and 10 degree sizes, the implant 1400 can be custom fit into disk spaces with varying degrees of lordosis. Lordosis is mainly generated by the disk height being higher anteriorly compared to the posterior end of the disk. At the anterior end of the disk space, there is a noticeable expansion in the disk height. By incorporating the flared tail portion, this anatomical feature can be used to increase stabilization of the implant 1400. The flared tail portion also facilitates to cut past the surfaces of adjacent vertebrae in the intervertebral disk cavity.

The inner surface of sidewall 1407A can include a pair of opposing channels (not shown) for secureably receiving a pair of slidable anchor plates 1410, 1415. A first end of the slidable anchor plates 1410, 1415 can include a beveled edge to facilitate cutting into the surfaces of adjacent vertebrae in the intervertebral disk cavity. A second end of each slidable anchor plates 1410, 1415 can include a semi-circular notch such that when the slidable anchor plates 1410, 1415 mate and substantially completely reside within the cage 1405, a cavity 1430 is defined between slidable anchor plates 1410 and 1415. The cage 1405 further includes a pair of hinged pins 1435A, 1435A'. The hinged pins 1435A, 1435A' can be attached to a bar (not shown) which can slide into a slot (not shown) on an inside surface of sidewall 1407A. The cage 1405 further includes a track 1440 for receiving an applicator.

In one embodiment, a method of performing LIDS includes placing the cage 1405 horizontally (as shown in FIG. 14A) between the surfaces of adjacent vertebrae in the intervertebral disk cavity. The cage 1405 is then rotated through 90 degrees (as shown in FIG. 14B) to a vertical position using an appropriate applicator. The applicator can be placed in track 1440.

Now referring to FIG. 14C, a self locking screw 1450 is inserted into the cavity 1430 formed between the slidable anchor plates 1410, 1415 using an appropriate applicator. The head of the self locking screw 1450 can be shaped appropriately, for example, it can be conical to push the slidable anchor plates 1410, 1415 apart. The self locking screw 1450 is dimensioned such that it has greater dimension than cavity 1430 such that it is locked securely in the cavity 1430 thereby preventing the slidable anchor plates 1410, 1415 from coming back together. The self locking screw 1450 includes a threaded portion on its head which can cut into the semi-circular notches of the slidable anchor plates 1410, 1415 and can be locked in position thereby preventing the self locking screw 1450 from coming out of the cavity. When the self locking screw 1450 is turned the slidable anchor plates 1410, 1415 can be distracted upwards and downwards respectively through the channel provided in the cage 1405. The slidable anchor plates 1410, 1415 can be configured to stop further movement upon reaching an end of a slot in the sliding path. This causes the beveled ends of the slidable anchor plates 1410, 1415 to cut into an upper and a lower vertebra in the intervertebral disk space. When the self locking screw 1450 is inserted in the cavity 1430, it can also cause the bar (on which the hinged pins 1435A, 1435A' are attached) to slide within a slot (not shown) on the inside surface of sidewall 1407A. The hinged pins 1435A, 1435A' can come out cutting into the surfaces of adjacent vertebrae in the intervertebral disk cavity.

Figure 14D:
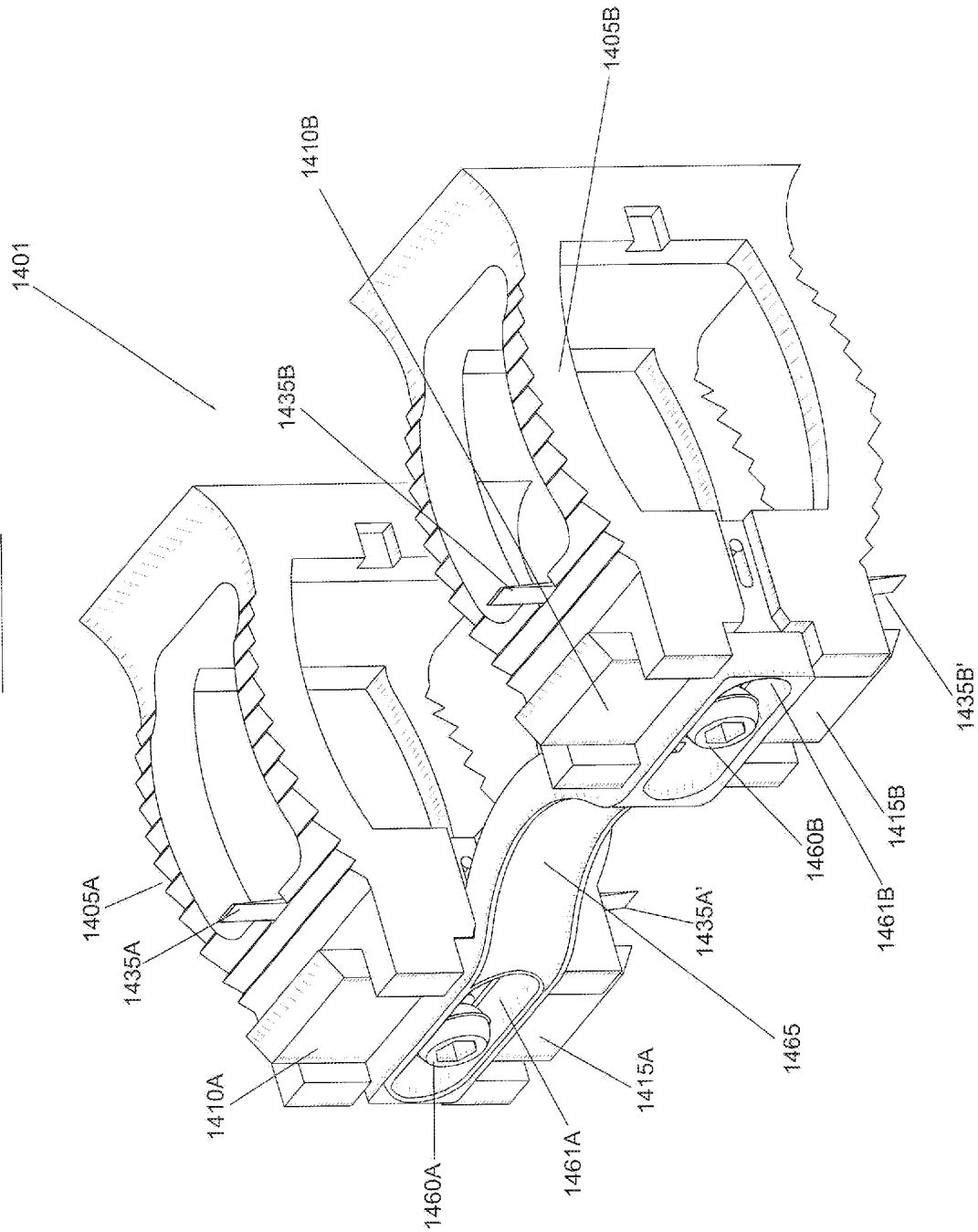
FIG. 14D is a perspective view of a connected intervertebral disk implant in its final position in accordance with a modified third embodiment of the invention.

FIG. 14D shows an exemplary embodiment of a connected implant 1401. The connected implant 1401 includes a pair of cages 1405A, 1405B. Cages 1405A, 1405B are substantially similar to cage 1400 described earlier. However, cages 1405A, 1405B differ from cage 1405 in that they are not independent. A connecting plate 1465 connects cages 1405A, 1405B which thereby causes them to act as a single interdependent unit. The self locking screws 1460A, 1460B can get locked in the connecting plate 1465 as opposed to between the slidable anchor plates 1410, 1415 in the case of cage 1405. Also, while one end of sliding plates 1410A, 1415A and 1410B, 1415B may terminate in a beveled edge, a second end may be substantially planar (and may be devoid of a semi-circular notch as in the case of sliding plates 1410, 1415).

In one embodiment, a method of performing LIDS includes placing cages 1405A, 1405B horizontally (not shown) between the surfaces of adjacent vertebrae in the intervertebral disk cavity. The cages 1405A, 1405B are then rotated through 90 degrees (as shown in FIG. 14D) to a vertical position using an appropriate applicator. As described with reference to FIG. 14C, the flared tail portion can cut past the bone in the intervertebral disk space. Using a device such as a screw driver, the slidable anchor plates 1410A, 1415A and 1410B, 1415B can be distracted upwards and downwards through a channel provided in the cages 1405A, 1405B. Connecting plate 1465 is placed into a slot (not shown) in the cages 1405A, 1405B such that slidable anchor plates 1410A, 1415A and 1410B, 1415B can be kept in a distracted position. The connecting plate 1465 can be provided with a curvature to accommodate the dural sac. After the connecting plate 1465 is positioned, screws 1460A, 1460B are inserted into openings 1461A, 1461B in the connecting plate 1465 such that they are locked in position. The openings also 1461A, 1461B in the connecting plate 1465 facilitate a desired intercage distance during surgery. The hinged pins 1435A, 1435A' and 1435B, 1435B' can also cut into the upper and lower vertebra in the intervertebral disk space thereby providing further stabilization to the cage 1405A, 1405B by substantially resisting the migration of the implant 1401 in the intervertebral disk space.

Figure 14F:
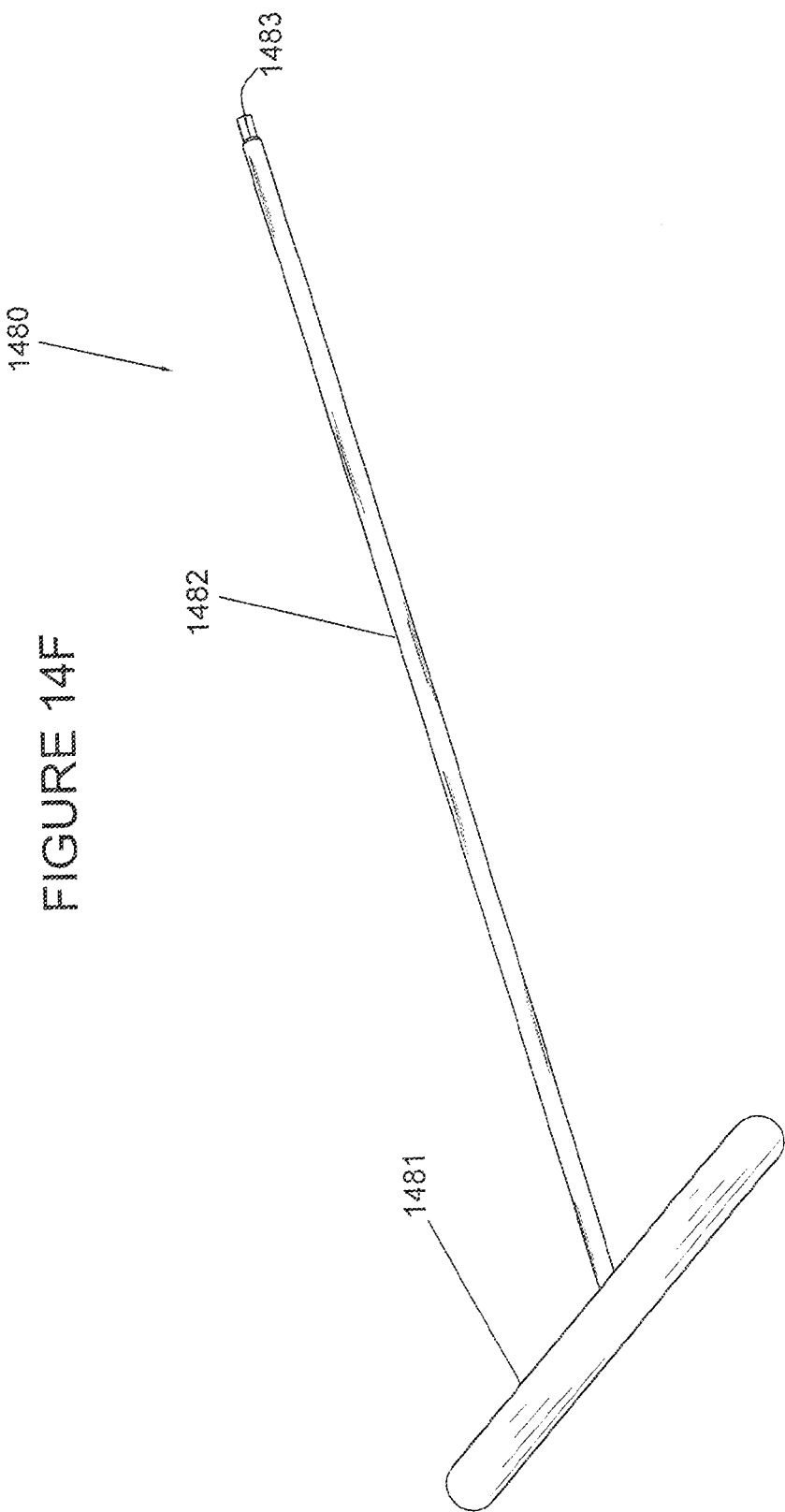
FIG. 14F is a perspective view of an applicator for the self locking screw in accordance with the third embodiment of the invention.

FIG. 14E shows an exemplary embodiment of an applicator 1470 for the cage 1405. FIG. 14F shows an exemplary embodiment of an applicator 1480 for the self locking screw 1450. FIG. 14G shows an exemplary embodiment of an applicator 1490 for the slidable anchor plates 1410, 1415. Each applicator 1470, 1480, 1495 includes a handle 1471, 1481, 1491 respectively. The handles 1471, 1481, 1491 can be coupled to an elongated shaft 1472, 1482, 1492 respectively. Each shaft 1472, 1482, 1492 terminates in a tip 1473, 1483, 1493 respectively. The tips 1473, 1483, 1493 can be shaped and dimensioned to receive the cage 1405, self locking screw 1450 and the slidable anchor plates 1410, 1415.

Those skilled in the art who have the benefit of this disclosure will recognize that it is advantageous to provide a kit comprised of a number of spreaders, depending upon the particular intervertebral disk cage and stabilizer being employed, of progressively larger diameters to obtain the desired degree of spread of the vertebrae adjacent the intervertebral disk space into which the implant (for example, 100A, 1300, 1301, 1400, 1401) is to be inserted. The kit contains spreaders of increasingly larger diameters in their respective expanded middle portions; it is also advantageous to supply spreaders in the kit having disk cage implant portions of different lengths. Likewise, it is advantageous to include in the kit, implants of different heights and widths to obtain the best fit between the anatomical region of the intervertebral disk space into which the implant is being inserted and the shape of the implant so as to be able to position the implant in the disk space at which the largest proportion of the sides of the disk cage implant bear against the surfaces of the bodies of the adjacent vertebrae, thereby maximizing the stabilizing properties of the implant.

The patient should be able to ambulate soon after the LIDS procedure because of the stability imparted to the spinal column by the implant of the present invention. Before narrowing of the disk space occurs, the cancellous bone chips will have started the fusion process. This procedure also prevents the narrowing of the disk space, which is a common problem with lateral intertransverse fusion.

Although primarily described in terms of the embodiments, it will be recognized by those skilled in the art that certain changes can be made to the specific structure of these various embodiments shown and described without departing from the spirit of the present invention. For instance, there are many ways other than those illustrated to mount the implant and anchor nail to the applicator for insertion into the intervertebral disk and rotation thereafter, while still enabling the applicator to be detached from the disk cage implant and anchor nail once positioned in the disk space, and all such structures are intended to fall within the scope of the present invention.

Likewise, implants having a slightly ovoid, or elliptical, cross-sectional shape while retaining the elongate, generally cylindrical shape of the implant are all intended to be encompassed within the scope of this invention. All such modifications, and other modifications which do not depart from the spirit of the present invention, are intended to fall within the scope of the following claims.

It should be understood that, as used herein, "first," "second," "third," etc., and "anterior" and "posterior" are arbitrarily assigned and are merely intended to differentiate between two or more sidewalls, positions, etc., as the case may be. Furthermore, it is to be understood that the mere use of the term "first" does not require that there be any "second," and the mere use of the term "second" does not require that there be any "third," etc.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is, therefore, evident that the particular illustrative embodiments disclosed above may be altered or modified and all such variations are considered within the scope and spirit of the present invention. While implant and methods are described in terms of "comprising," "containing," or "including" various components or steps, the compositions and methods also can "consist essentially of" or "consist of" the various components and steps. In particular, every range of values (of the form, "from about a to about b," or, equivalently, "from approximately a to b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an", as used in the claims, are defined herein to mean one or more than one of the element that it introduces. If there is any conflict in the usages of a word or term in this specification and one or more patent(s) or other documents that may be incorporated herein by reference, the definitions that are consistent with this specification should be adopted.

What is claimed is:

1. An intervertebral disk implant comprising:
   (A) a biconvex cage, the cage comprising:
      a first pair of opposing sidewalls, wherein the first pair of sidewalls includes a middle portion that is substantially expanded, and wherein the first pair of sidewalls terminates in a flared anterior end; and
      an upper sidewall and a lower sidewall, wherein each of the upper sidewall, the lower sidewall and the first pair of sidewalls comprises an opening therewith to define an internal fenestrated channel;
   (B) an upper and a lower anchor plate positioned along a posterior end of the cage, wherein the anchor plates are slidable for stabilizing the cage in an intervertebral disk space between a pair of adjacent vertebrae; and
   (C) a self-locking screw dimensioned to be inserted within a cavity defined by a corresponding notch in each of the upper and lower anchor plates,
      wherein upon turning the self-locking screw within the cavity, the upper and the lower anchor plates are distracted upwards and downwards respectively,
      wherein the upper and lower anchor plates slide within a posteriorly open notch formed by the cage, and
      wherein the implant further comprises an upper and a lower fixed pin located at the posterior end of the cage, and wherein the upper and lower fixed pins are positioned substantially adjacent the upper and lower anchor plates respectively.

2. The implant according to claim 1, wherein a height of the implant is greater at the flared anterior end as compared to a height of the implant at the posterior end.

3. The implant according to claim 1, wherein the upper and lower fixed pins are larger than serrations on the substantially expanded middle portion of the first pair of opposing sidewalls, and wherein the upper and lower fixed pins comprise a beveled end for cutting into the pair of adjacent vertebrae.

4. A connected intervertebral disk implant comprising:
   (A) first and second biconvex cages, each cage comprising:
      a first pair of opposing sidewalls, wherein the first pair of sidewalls includes a middle portion that is substantially expanded, and wherein the first pair of sidewalls terminates in a flared anterior end; and
      an upper sidewall and a lower sidewall, wherein each of the upper sidewall, the lower sidewall and the first pair of sidewalls comprises an opening therewith to define an internal fenestrated channel;
   (B) an upper and a lower anchor plate positioned along a posterior end of each of the first and the second cages, wherein the anchor plates are slidable for stabilizing the first and the second cages in an intervertebral disk space between a pair of adjacent vertebrae;
   (C) a connecting plate for coupling the first and second cages; and (D) a self-locking screw dimensioned to be inserted within a cavity defined by a corresponding notch in each of the upper and lower anchor plates in each of the first and second cages, wherein upon turning the self-locking screw within the cavity, the upper and the lower anchor plates are distracted upwards and downwards respectively, wherein a height of each of the first and the second cage is greater at the flared anterior end in comparison to a height of the first and the second cage at the posterior end, wherein the upper and lower anchor plates slide within a posteriorly open notch formed by each of the first and the second cages, and wherein the implant further comprises an upper and a lower fixed pin located at the posterior end of each of the first and second cages, and wherein the upper and lower fixed pins are positioned substantially adjacent the upper and lower anchor plates respectively.

5. The connected implant according to claim 4, wherein the flared anterior end of each of the first and the second cages further comprises a depression to prevent migration of the corresponding cage when the implant is positioned in the intervertebral disk space.

6. The connected implant according to claim 5, wherein the upper and lower fixed pins are larger than serrations on the substantially expanded middle portion of the first pair of opposing sidewalls, and wherein the fixed pins comprise a beveled end for cutting into the pair of adjacent vertebrae.

7. A method of stabilizing two adjacent vertebrae of a patient's spine after removal of a portion of an intervertebral disk to form a disk space therebetween comprising the steps of:

providing an intervertebral disk implant according to claim 1; inserting the implant into the disk space of the patient so that a width dimension of the implant is parallel to a longitudinal axis of the patient's spine;

rotating the implant approximately 90 degrees in the disk space so that a height dimension is parallel to the longitudinal axis of the patient's spine; and turning the self-locking screw to distract the upper and lower anchor plates, wherein each of the upper and lower and lower anchor plates has one or more surfaces for engaging the adjacent vertebrae to prevent rotation of the implant relative to the body of the adjacent vertebrae.

8. The method according to claim 7, further comprising mounting an applicator to one end of the cage before inserting the cage into the disk space.

9. The method according to claim 8, wherein the cage is rotated by rotating the applicator.

* * * * *